(12) United States Patent
de Raad et al.

(10) Patent No.: US 11,339,434 B2
(45) Date of Patent: May 24, 2022

(54) METHODS FOR DETERMINING GENE FUNCTIONS

(71) Applicant: The Regents of the University of California, Oakland, CA (US)

(72) Inventors: Markus de Raad, Berkeley, CA (US); Trent R. Northen, Walnut Creek, CA (US); Curt R. Fischer, Mountain View, CA (US)

(73) Assignee: The Regents of the University of California, Oakland, CA (US)

( * ) Notice: Subject to any disclaimer, the term of this patent is extended or adjusted under 35 U.S.C. 154(b) by 321 days.

(21) Appl. No.: 15/663,528

(22) Filed: Jul. 28, 2017

(65) Prior Publication Data

US 2018/0030531 A1    Feb. 1, 2018

Related U.S. Application Data

(60) Provisional application No. 62/462,268, filed on Feb. 22, 2017, provisional application No. 62/368,887, filed on Jul. 29, 2016.

(51) Int. Cl.
| | |
|---|---|
| *C12Q 1/68* | (2018.01) |
| *C12Q 1/25* | (2006.01) |
| *G01N 33/573* | (2006.01) |
| *C12N 15/10* | (2006.01) |
| *C12P 21/06* | (2006.01) |
| *C12Q 1/6872* | (2018.01) |

(52) U.S. Cl.
CPC .......... *C12Q 1/6872* (2013.01); *C12N 15/10* (2013.01); *C12P 21/06* (2013.01); *C12Q 1/25* (2013.01); *G01N 33/573* (2013.01)

(58) Field of Classification Search
None
See application file for complete search history.

(56) References Cited

U.S. PATENT DOCUMENTS

| | | | | |
|---|---|---|---|---|
| 6,136,961 A | * | 10/2000 | Dordick | C07D 305/14 536/17.2 |
| 9,273,308 B2 | * | 3/2016 | Link | B01F 3/0807 |
| 2002/0046948 A1 | * | 4/2002 | Chow | B01J 19/0093 204/450 |
| 2002/0076739 A1 | * | 6/2002 | Aebersold | C12Q 1/25 435/7.92 |
| 2002/0137057 A1 | * | 9/2002 | Wold | C12Q 1/6872 435/6.1 |
| 2006/0078888 A1 | * | 4/2006 | Griffiths | B01F 3/0807 435/6.11 |
| 2008/0168572 A1 | * | 7/2008 | Stetter | C07K 14/195 800/8 |
| 2009/0233806 A1 | * | 9/2009 | Carr | G01N 33/6845 506/9 |
| 2010/0151439 A1 | * | 6/2010 | Pamula | B01F 13/0809 435/4 |
| 2013/0296192 A1 | * | 11/2013 | Jacobson | B01J 19/0046 506/11 |
| 2015/0315570 A1 | * | 11/2015 | Zhao | C12N 15/66 506/14 |
| 2018/0284125 A1 | * | 10/2018 | Gordon | C12Q 1/6874 |

OTHER PUBLICATIONS

Pi et al., J. Am. Soc. Mass Spectrom., 15:233-243 (2004) (Year: 2004).*
Lee et al., J. Mass. Spectrom., 44:579-593 (2009) (Year: 2009).*
Cancilla et al., PNAS, 97(22):12008-12013 (2000) (Year: 2000).*
De Rond et al., Curr. Op. Biotechnol., 31:1-9 (2015) (Year: 2015).*
Duriez et al., J. Proteome Res., 14:728-737 (2015) (Year: 2015).*
Kuster et al., Anal. Chem., 85:1285-1289 (2013) (Year: 2013).*
Nguyen et al., Proteomics Clin/ Appl., 8:737-747 (2014) (Year: 2014).*
Romero et al., PNAS, 112(23):7159-7164 (2015) (Year: 2015).*
Wigle et al., J. Biomolec. Screening, 20(6):810-820 (2015) (Year: 2015).*
Gale et al., LCGC North Am., 33(1):34-41 (2015) (Year: 2015).*
Schaffrath et al., EuPA Open Proteomics, 3:239-245 (2014) (Year: 2014).*
Thompson et al., Anal. Chem., 75:1895-1904 (2003) (Year: 2003).*
Zhang et al., Meth. Mol Biol., 673:211-222 (2010) (Year: 2010).*
Anton et al., "Objective: biochemical function," Frontiers in Genetics 2014, 5(210), 1-4.
Bastard et al., "Revealing the hidden functional diversity of an enzyme family," Nature Chemical Biology 2014, 10, 42-49.
Greving et al., "Acoustic deposition with NIMS as a high-throughput enzyme activity assay," Analytical Bioanalytical Chemistry 2012, 1-5.
Heins et al., "Phylogenomically Guided Identification of Industrially Relevant GH1 β-Glucosidases through DNA Synthesis and Nanostructure-Initiator Mass Spectrometry," American Chemical Society 2014, 9, 2083-2091.
Korman et al., "A synthetic biochemistry system for the in vitro production of isoprene from glycolysis intermediates," The Protein Society 2014, 23, 576-585.
Northen et al., "Clathrate nanostructures for mass spectrometry," Nature 2007, 449, 1033-1036.
Northen et al., "A nanostructure-initiator mass spectrometry-based enzyme activity assay," PNAS 2008, 105(10), 3678-3683.
Rübel et al., "OpenMSI: A High-Performance Web-Based Platform for Mass Spectrometry Imaging," Analytical Chemistry 2013, 85, 10354-10361.

(Continued)

*Primary Examiner* — Michelle F. Paguio Frising

(74) *Attorney, Agent, or Firm* — Sheppard, Mullin, Richter & Hampton LLP

(57) ABSTRACT

Disclosed herein are methods, systems and compositions for determining substrate specificity of an enzyme. The disclosed methods, systems and compositions can be used for identifying enzymes capable of modifying substrates of interest and/or quantifying enzymatic activity.

16 Claims, 9 Drawing Sheets

Specification includes a Sequence Listing.

(56) References Cited

OTHER PUBLICATIONS

Sorokina et al., "Profiling the orphan enzymes," Biology Direct 2014, 9(10), 1-16.
Temperton et al., "Metagenomics: microbial diversity through a scratched lens," Current Opinion in Microbiology 2012, 15, 605-612.
Yao et al., "Analysis of Metabolomics Datasets with High-Performance Computing and Metabolite Atlases," Metabolites 2015, 5, 431-442.

* cited by examiner

METHODS FOR DETERMINING GENE FUNCTIONS

RELATED APPLICATIONS

The present application claims priority under 35 U.S.C. § 119(e) to U.S. Provisional Application No. 62/368,887, filed on Jul. 29, 2016; and U.S. Provisional Application No. 62/462,268, filed on Feb. 22, 2017. The content of these related applications is hereby expressly incorporated by reference in its entirety.

STATEMENT REGARDING FEDERALLY SPONSORED R&D

This invention was made with government support under grant No. DE-AC02-05CH11231 awarded by the U.S. Department of Energy. The government has certain rights in the invention.

REFERENCE TO SEQUENCE LISTING

The present application is being filed along with a Sequence Listing in electronic format. The Sequence Listing is provided as a file entitled Sequence_Listing_LBNL_071A.txt, created Jul. 17, 2017, which is 26,286 bytes in size. The information in the electronic format of the Sequence Listing is incorporated herein by reference in its entirety.

BACKGROUND

Field

The present disclosure relates generally to the field of molecular biology, and more particularly to determining the identity and the activity of gene products.

Description of the Related Art

Methods and techniques based on liquid chromatography-mass spectrometry (LC-MS) have been developed to determine the activities of enzymes. Methods and techniques based on spectroscopy have been developed to determine the substrates of enzymes. However, these methods and techniques do not have multiplex capability. Thus, there is a need for high throughput methods and systems capable of determining the identity and the activity of gene products.

SUMMARY

Disclosed herein are methods for determining substrate specificity of an enzyme. In some embodiments, the methods comprise: providing a sample comprising a barcoded enzyme, wherein the barcoded enzyme comprises the enzyme cleavably fused to a barcode (e.g., a peptide barcode); incubating the barcoded enzyme with a protease capable of removing the peptide barcode from the barcoded enzyme and one or more candidate substrates to obtain one or more modified candidate substrates in one or more reactions; generating a mass spectrum of each of the one or more reactions; determining a substrate specificity of the enzyme with respect to each of the one or more candidate substrates based on the mass spectrum; and determining the identity of the barcoded enzyme in the sample by identifying peptide barcode ions in the mass spectrum.

In some embodiments, determining the substrate specificity of the enzyme with respect to each of the one or more candidate substrates is based on whether ions of each of the one or more modified candidate substrates are in the mass spectrum. In some embodiments, determining the substrate specificity of the enzyme with respect to each of the one or more candidate substrates is based on the ratio of ions of each of the one or more candidate substrates and ions of a corresponding modified candidate substrate in the mass spectrum.

In some embodiments, incubating the barcoded enzyme with the protease and the one or more candidate substrates comprises adding the barcoded enzyme into a solution, wherein the solution comprises the protease and the one or more candidate substrates. The barcoded enzyme is incubated with the protease prior to being incubated with the one or more candidate substrates or is incubated with the protease after being incubated with the one or more candidate substrates.

In some embodiments, the barcoded enzyme is incubated with some or all of the one or more candidate substrates in one of the one or more reactions. In some embodiments, the barcoded enzyme is incubated with one of the one or more candidate substrates in one of the one or more reactions. In some embodiments, volume of at least one of the one or more reactions is about 1 microliter, about 1 nanoliter, or about 1 picoliter.

In some embodiments, providing the sample comprising the barcoded enzyme comprises: providing a polynucleotide encoding the barcoded enzyme; and incubating the polynucleotide in a cell-free transcription/translation reaction to generate the barcoded enzyme. In some embodiments, providing the sample comprises providing the barcoded enzyme using a microfluidic device. Providing the barcoded enzyme can comprise: generating a first droplet comprising a polynucleotide encoding the barcoded enzyme using a first microchannel of the microfluidic device; generating a second droplet comprising components of a cell-free transcription/translation reaction using a second microchannel of the microfluidic device; generating a first combined droplet comprising the polynucleotide and the components of the cell-free transcription/translation reaction from the first droplet and the second droplet using an immiscible fluid; and incubating the polynucleotide with the components of the cell-free transcription/translation reaction to generate the barcoded enzyme in the first combined droplet. The components of the cell-free transcription/translation reaction can comprise a reaction buffer, a RNA polymerase, nucleotide triphosphates (NTPs), a ribonuclease inhibitor, a ribosome, aminoacyl-tRNA synthetase, tRNA, an amino acid mixture, an initiation factor, an elongation factor, a release factor, or a combination thereof. Incubating the barcoded enzyme with the one or more candidate substrates can comprise incubating the barcoded enzyme with the one or more candidate substrates using the microfluidic device. Incubating the barcoded enzyme with the one or more candidate substrates using the microfluidic device can comprise: generating a third droplet comprising the one or more candidate substrates using a third microchannel of the microfluidic device; generating a second combined droplet comprising the barcoded enzyme and the one or more candidate substrates from the first combined droplet and the third droplet using the immiscible fluid; and incubating the barcoded enzyme with the one or more candidate substrates in the second combined droplet.

In some embodiments, incubating the barcoded enzyme with the one or more candidate substrates comprises incubating the barcoded enzyme with the one or more candidate substrates using a microfluidic device. Incubating the barcoded enzyme with the one or more candidate substrates using the microfluidic device can comprise: generating a first droplet comprising the barcoded enzyme using a first microchannel of the microfluidic device; generating a second droplet comprising the one or more candidate substrates using a second microchannel of the microfluidic device; generating a first combined droplet comprising the barcoded enzyme and the one or more candidate substrates from the first droplet and the second droplet using an immiscible fluidic; and incubating the barcoded enzyme with the one or more candidate substrates in the first combined droplet. The immiscible fluid can comprise oil. In some embodiments, the barcoded enzyme is produced in a cell-based expression system such as an *E. coli* expression system.

In some embodiments, the mass spectrum is generated using soft ionization mass spectrometry (MS), such as matrix associated laser desorption ionization (MALDI-MS) and nanostructure-initiator MS (NIMS). In some embodiments, the mass spectrum is generated using electrospray ionization MS (ESI-MS), liquid chromatography ESI-MS, nanostructure-initiator MS, fast atom bombardment MS, chemical ionization MS, atmospheric-pressure chemical ionization MS, matrix-assisted laser desorption/ionization MS, or any combination thereof.

In some embodiments, the one or more candidate substrates differ from one another by at least one functional group. In some embodiments, some candidate substrates differ from one another by at least one function group. In some embodiments, each of the one or more candidate substrates differ from its corresponding modified candidate substrate by at least one functional group. In some embodiments, some candidate substrates differ from their corresponding modified candidate substrates by at least one functional group. The at least one functional group is alkyl, alkynyl, alkenyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, or borinate.

In some embodiments, the enzyme is a methyltransferase or a glycoside hydrolase. In some embodiments, the enzyme is a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, or a xylosidase.

In some embodiments, at least one of the one or more candidate substrates is 6-mercaptopurine, cellobiose, cellotetraose, xylotetraose, isoprimeverose, β-D-gentiobiose, xyloglucan, mannotriose, or any combination thereof. In some embodiments, the one or more candidate substrate is agarose, amino acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof.

In some embodiments, the one or more candidate substrates comprise at least 10, at least 100, or at least 1000 substrates.

Disclosed herein are methods for identifying an enzyme capable of modifying a substrate of interest. In some embodiments, the methods comprise: providing one or more barcoded enzymes, wherein each of the barcoded enzymes is cleavably fused to a barcode (e.g., a peptide barcode); incubating the one or more barcoded enzymes with a protease capable of removing the peptide barcode from the one or more barcoded enzymes and the substrate of interest to obtain a modified substrate of interest in one or more reactions; generating a mass spectrum of each of the one or more reactions; and determining the activity of each of the one or more barcoded enzymes with respect to the substrate of interest based on the mass spectrum.

In some embodiments, incubating the barcoded enzymes with the protease and the substrate of interest comprises incubating two or more barcoded enzymes with the protease and the substrate of interest. In some embodiments, the two or more barcoded enzymes comprise at least 10, 100, or 1000 barcoded enzymes.

In some embodiments, determining an activity of each of the one or more barcoded enzymes is based on whether ions of the modified substrate of interest are in the mass spectrum. Determining the activity of each of the one or more barcoded enzymes is based on the ratio of the substrate of interest ions and the modified substrate of interest ions in the mass spectrum.

In some embodiments, incubating the one or more barcoded enzymes with the protease and the substrate of interest comprises adding the barcoded enzymes into a solution, wherein the solution comprises the protease and the substrate of interest. The one or more barcoded enzymes are incubated with the protease prior to being incubated with the substrate of interest. The one or more barcoded enzymes are incubated with the protease after being incubated with the substrate of interest.

In some embodiments, some or all of the barcoded enzymes are incubated with the substrate of interest in one of the one or more reactions. In some embodiments, one of the one or more barcoded enzymes is incubated with the substrate of interest in one of the one or more reactions. In some embodiments, volume of at least one of the one or more reactions is about 1 microliter, about 1 nanoliter, or about 1 picoliter.

In some embodiments, providing the one or more barcoded enzymes comprises: providing polynucleotides each encoding one of the one or more barcoded enzymes; and incubating the polynucleotides in a cell-free transcription/translation reaction to generate the one or more barcoded enzymes. In some embodiments, providing the one or more barcoded enzymes comprises providing the one or more barcoded enzymes using a microfluidic device. Providing the one or more barcoded enzyme can comprise: generating a first droplet comprising one or more polynucleotides encoding the one or more barcoded enzymes using a first microchannel of the microfluidic device; generating a second droplet comprising components of a cell-free transcription/translation reaction using a second microchannel of the microfluidic device; generating a first combined droplet comprising the one or more polynucleotides and the components of the cell-free transcription/translation reaction from the first droplet and the second droplet using an immiscible fluid; and incubating the one or more polynucleotides with the components of the cell-free transcription/translation reaction to generate the barcoded enzyme in the first combined droplet. The components of the cell-free transcription/translation reaction can comprise a reaction buffer, a RNA polymerase, nucleotide triphosphates (NTPs), a ribonuclease inhibitor, a ribosome, aminoacyl-tRNA synthetase, tRNA, an amino acid mixture, an initiation factor, an elongation factor, a release factor, or a combination thereof. Incubating the one or more barcoded enzymes with the substrate of interest can comprise incubating the one or more barcoded enzymes with the substrate of interest using the microfluidic device. Incubating the one or more barcoded enzymes with the substrate of interest using the microfluidic device can comprise: generating a third droplet comprising the substrate of interest using a third microchannel of the microfluidic device; generating a second combined droplet comprising the one or more barcoded enzymes and the substrate of interest from the first combined droplet and the third droplet using the immiscible fluidic; and incubating the one or more barcoded enzymes with the substrate of interest in the second combined droplet.

In some embodiments, incubating the one or more barcoded enzymes with the substrate of interest comprises incubating the one or more barcoded enzymes with the substrate of interest using a microfluidic device. Incubating the one or more barcoded enzymes with the substrate of interest using the microfluidic device can comprise: generating a first droplet comprising the one or more barcoded enzymes using a first microchannel of the microfluidic device; generating a second droplet comprising the substrate of interest using a second microchannel of the microfluidic device; generating a first combined droplet comprising the one or more barcoded enzymes and the substrate of interest from the first droplet and the second droplet using an immiscible fluidic; and incubating the one or more barcoded enzymes with the substrate of interest in the first combined droplet. The immiscible fluid can comprise oil. In some embodiments, one of the one or more barcoded enzymes is produced in a cell-based expression system such as an *E. coli* expression system.

In some embodiments, the mass spectrum is generated using soft ionization mass spectrometry (MS), matrix associated laser desorption ionization (MALDI-MS) and nanostructure-initiator MS (NIMS). In some embodiments, the mass spectrum is generated using electrospray ionization MS (ESI-MS), liquid chromatography ESI-MS, nanostructure-initiator MS, fast atom bombardment MS, chemical ionization MS, atmospheric-pressure chemical ionization MS, matrix-assisted laser desorption/ionization MS, or any combination thereof.

In some embodiments, the substrate of interest differs from the modified substrate of interest by at least one functional group. In some embodiments, the one at least one functional group is alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, borinate groups, or any combination thereof.

Disclosed herein are methods for quantifying enzymatic activity. In some embodiments, the methods comprise: providing one or more barcoded enzymes, wherein each of the one or more barcoded enzymes is cleavably fused to a first peptide barcode; for each of the one or more barcoded enzymes: incubating the barcoded enzyme with a protease capable of removing the peptide barcode from the barcoded enzyme and a candidate substrate to obtain a modified candidate substrate in a reaction; generating a mass spectrum of the reaction; quantifying the barcoded enzyme in the reaction based on the mass spectrum; and quantifying the enzymatic activity of the barcoded enzymes with respect to the candidate substrate based on the ratio of the candidate substrate and the modified candidate substrate in the mass spectrum.

In some embodiments, the one or more barcoded enzymes comprise at least 10, at least 100, or at least 1000 barcoded enzymes. In some embodiments, quantifying the barcoded enzyme is based on the first peptide barcode ions in the mass spectrum.

In some embodiments, each of the barcoded enzymes is further cleavably fused to a second peptide barcode, the protease is capable of removing the second peptide barcode from each of the barcoded enzymes, and quantifying the barcoded enzyme is based on the second peptide barcode ions in the mass spectrum.

In some embodiments, the barcoded enzyme is incubated with the protease and the candidate substrate simultaneously. In some embodiments, the barcoded enzyme is incubated with the protease prior to being incubated with the candidate substrate. In some embodiments, the barcoded enzyme is incubated with the protease subsequent to being incubated with the candidate substrate.

In some embodiments, volume of the reaction is about 1 microliter, about 1 nanoliter, or about 1 picoliter. In some embodiments, each of the one or more barcoded enzymes is incubated with the protease subsequent to being incubated with the candidate substrate.

In some embodiments, providing the one or more barcoded enzymes comprises: for each of the one or more barcoded enzymes: generating a polynucleotide encoding the barcoded enzyme; and incubating the polynucleotide in a cell-free transcription/translation reaction. In some embodiments, providing the one or more barcoded enzymes comprises providing the one or more barcoded enzymes using a microfluidic device. Providing the one or more barcoded enzyme can comprise: for the each of the one or more barcoded enzymes: generating a first droplet comprising a polynucleotide encoding the barcoded enzyme using a first microchannel of the microfluidic device; generating a second droplet comprising components of a cell-free transcription/translation reaction using a second microchannel of the microfluidic device; generating a first combined droplet comprising the polynucleotide and the components of the cell-free transcription/translation reaction from the first droplet and the second droplet using an immiscible fluid; and incubating the polynucleotide with the components of the cell-free transcription/translation reaction to generate the barcoded enzyme in the first combined droplet. The components of the cell-free transcription/translation reaction can comprise a reaction buffer, a RNA polymerase, nucleotide triphosphates (NTPs), a ribonuclease inhibitor, a ribosome, aminoacyl-tRNA synthetase, tRNA, an amino acid mixture, an initiation factor, an elongation factor, a release factor, or a combination thereof. Incubating the barcoded enzyme with the candidate substrate can comprise incubating the barcoded enzyme with the candidate substrate using the microfluidic device. Incubating the barcoded enzymes with the candidate substrate using the microfluidic device can comprise: generating a third droplet comprising the candidate substrate using a third microchannel of the microfluidic device; generating a second combined droplet comprising the barcoded enzyme and the candidate substrate from the first combined droplet and the third droplet using the immiscible fluidic; and incubating the barcoded enzyme with the candidate substrate in the second combined droplet.

In some embodiments, incubating the barcoded enzyme with the candidate substrate comprises incubating the barcoded enzyme with the candidate substrate using a microfluidic device. Incubating the barcoded enzyme with the candidate substrate using the microfluidic device can comprise: generating a first droplet comprising the barcoded enzyme using a first microchannel of the microfluidic device; generating a second droplet comprising the candidate substrate using a second microchannel of the microfluidic device; generating a first combined droplet comprising the barcoded enzyme and the candidate substrate from the first droplet and the second droplet using an immiscible fluidic; and incubating the barcoded enzyme with the candidate substrate in the first combined droplet. The immiscible fluid can comprise oil. In some embodiments, the one or more barcoded enzymes are produced in a cell-based expression system, such as an *E. coli* expression system.

In some embodiments, the mass spectrum is generated using soft ionization mass spectrometry matrix associated laser desorption ionization (MALDI-MS) and nanostructure-initiator MS (NIMS). In some embodiments, the mass spectrum is generated using electrospray ionization MS (ESI-MS), liquid chromatography ESI-MS, nanostructure-initiator MS, fast atom bombardment MS, chemical ionization MS, atmospheric-pressure chemical ionization MS, matrix-assisted laser desorption/ionization MS, or any combination thereof.

In some embodiments, the candidate substrate differs from the modified candidate substrate by at least one functional group. In some embodiments, the at least one functional group is: alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, borinate groups, or any combination thereof.

Also disclosed herein are methods for determining activities of a number of enzymes. In some embodiments, the methods comprise: providing a first barcoded enzyme and a second non-barcoded enzyme, wherein the first barcoded enzyme is cleavably fused to a barcode (e.g., a peptide barcode); incubating the first barcoded enzyme and the second non-barcoded enzyme with a protease capable of removing the peptide barcode from the first barcoded enzyme and one or more candidate substrates to obtain one or more modified candidate substrates in one or more reactions; generating a mass spectrum of each of the one or more reactions; determining the activities of the first barcoded enzyme and the second non-barcoded enzyme with respect to each of the one or more candidate substrates based on the mass spectrum; and determining the identities of the barcoded enzyme and the second non-barcoded enzyme by identifying peptide barcode ions in the mass spectrum.

In some embodiments, the first barcoded enzyme and the second non-barcoded enzyme are involved in the same metabolic pathway. In some embodiments, determining the activities of the first barcoded enzyme and the second non-barcoded enzyme with respect to each of the one or more candidate substrates is based on whether ions of each of the one or more modified candidate substrates are in the mass spectrum. In some embodiments, determining the activities of the first barcoded enzyme and the second non-barcoded enzyme with respect to each of the one or more candidate substrates is based on the ratio of ions of each of the one or more candidate substrates and ions of a corresponding modified candidate substrate in the mass spectrum.

In some embodiments, incubating the first barcoded enzyme and the second non-barcoded enzyme with the protease and the one or more candidate substrates comprises adding the first barcoded enzyme and the second non-barcoded enzyme into a solution, wherein the solution comprises the protease and the one or more candidate substrates. In some embodiments, the first barcoded enzyme and the second non-barcoded enzyme are incubated with the protease prior to being incubated with the one or more candidate substrates. In some embodiments, the first barcoded enzyme and the second non-barcoded enzyme are incubated with the protease after being incubated with the one or more candidate substrates.

In some embodiments, providing the first barcoded enzyme and the second non-barcoded enzyme comprises: providing a polynucleotide encoding the first barcoded enzyme and the second non-barcoded enzyme; and incubating the polynucleotide in a cell-free transcription/translation reaction to generate the first barcoded enzyme and the second non-barcoded enzyme. In some embodiments, providing the first barcoded enzyme and the second non-barcoded enzyme comprises: providing a first polynucleotide encoding the first barcoded enzyme; providing a second polynucleotide encoding the second non-barcoded enzyme; and incubating the first polynucleotide and the second polynucleotide in a cell-free transcription/translation reaction to generate the first barcoded enzyme and the second non-barcoded enzyme.

In some embodiments, providing the first barcoded enzyme and the second non-barcoded enzyme comprises providing the first barcoded enzyme and the second non-barcoded enzyme using a microfluidic device. Providing the first barcoded enzyme and a second non-barcoded enzyme can comprise: generating a first droplet comprising a first polynucleotide encoding the first barcoded enzyme and a second polynucleotide encoding the second non-barcoded enzyme using a first microchannel of the microfluidic device; generating a second droplet comprising components of a cell-free transcription/translation reaction using a second microchannel of the microfluidic device; generating a first combined droplet comprising the first polynucleotide and the second polynucleotide and the components of the cell-free transcription/translation reaction from the first droplet and the second droplet using an immiscible fluid; and incubating the first polynucleotide and the second polynucleotide with the components of the cell-free transcription/translation reaction to generate the first barcoded enzyme and the second non-barcoded enzyme in the first combined droplet. The components of the cell-free transcription/translation reaction can comprise a reaction buffer, a RNA polymerase, nucleotide triphosphates (NTPs), a ribonuclease inhibitor, a ribosome, aminoacyl-tRNA synthetase, tRNA, an amino acid mixture, an initiation factor, an elongation factor, a release factor, or a combination thereof. Incubating the first barcoded enzyme and the second non-barcoded enzyme with the one or more candidate substrates can comprise incubating the first barcoded enzyme and the second non-barcoded enzyme with the one or more candidate substrates using the microfluidic device. Incubating the first barcoded enzyme and the second non-barcoded enzyme with the one or more candidate substrates using the microfluidic device can comprise: generating a third droplet comprising the one or more candidate substrates using a third microchannel of the microfluidic device; generating a second combined droplet comprising the first barcoded enzyme, the second non-barcoded enzyme, and the one or more candidate substrates from the first combined droplet and the third droplet using the immiscible fluidic; and incubating the first barcoded enzyme and the second non-barcoded enzyme with the one or more candidate substrates in the second combined droplet.

In some embodiments, incubating the first barcoded enzyme and the second non-barcoded enzyme with the one or more candidate substrates comprises incubating the first barcoded enzyme and the second non-barcoded enzyme with the one or more candidate substrates using a microfluidic device. Incubating the first barcoded enzyme and the second non-barcoded enzyme with the one or more candidate substrates using the microfluidic device can comprise: generating a first droplet comprising the first barcoded enzyme and the second barcoded enzyme using a first microchannel of the microfluidic device; generating a second droplet comprising the one or more candidate substrates using a second microchannel of the microfluidic device; generating a first combined droplet comprising the first barcoded enzyme, the second non-barcoded enzyme, and the one or more candidate substrates from the first droplet and the second droplet using an immiscible fluidic; and incubating the first barcoded enzyme and the second non-barcoded enzyme with the one or more candidate substrates in the first combined droplet. The immiscible fluid can comprise oil. In some embodiments, the first barcoded enzyme and the second barcoded enzyme are produced together in a cell-based expression system, for example an *E. coli* expression system.

In some embodiments, the mass spectrum is generated using soft ionization mass spectrometry (MS) matrix associated laser desorption ionization (MALDI-MS) and nanostructure-initiator MS (NIMS). In some embodiments, the mass spectrum is generated using electrospray ionization MS (ESI-MS), liquid chromatography ESI-MS, nanostructure-initiator MS, fast atom bombardment MS, chemical ionization MS, atmospheric-pressure chemical ionization MS, matrix-assisted laser desorption/ionization MS, or any combination thereof.

In some embodiments, the one or more candidate substrates differ from one another by at least one functional group. Each of the one or more candidate substrates differ from its corresponding modified candidate substrate by at least one functional group. The at least one functional group is alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, or borinate.

In some embodiments, the first barcoded enzyme or the second non-barcoded enzyme is a methyltransferase or a glycoside hydrolase. The first barcoded enzyme or the second-barcoded enzyme is a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, or a xylosidase.

In some embodiments, at least one of the one or more candidate substrates is 6-mercaptopurine, cellobiose, cellotetraose, xylotetraose, isoprimeverose, β-D-gentiobiose, xyloglucan and mannotriose, or any combination thereof. At least one of the one or more candidate substrate is agarose, amino acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof. The one or more candidate substrates comprise at least 10 substrates, 100 substrates, or 1000 substrates.

DETAILED DESCRIPTION

Figure 1:
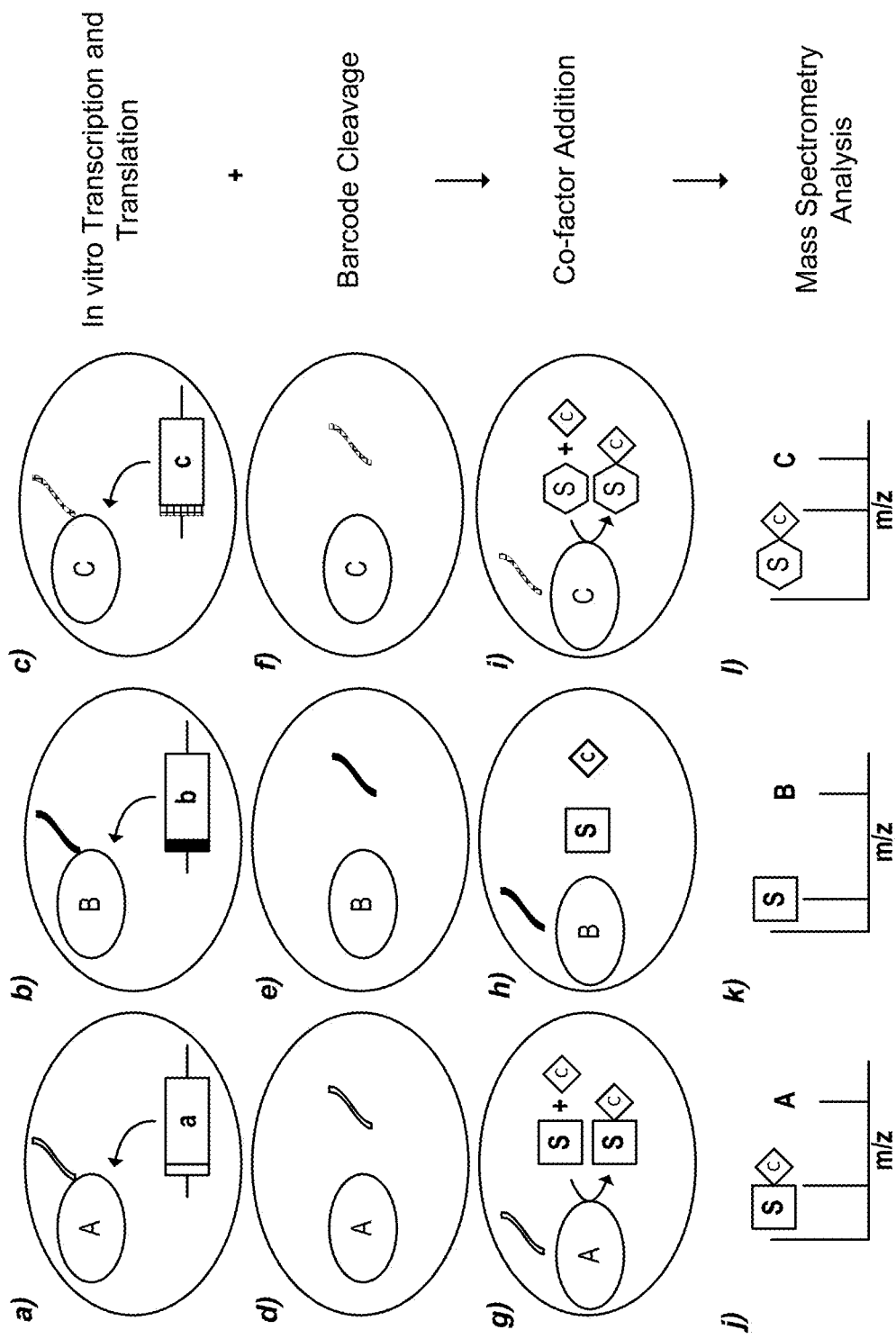
FIG. 1 is a non-limiting exemplary schematic illustration of a method for enzyme identification according to the scope of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, NY 1989).

Disclosed herein are systems and methods for efficient and scalable determination of gene functions by quickly and reliably determining the functions of putative proteins (e.g., enzymes). In some embodiments, the methods and systems are used for assignment of the reactions of gene products in organisms. The functions of putative proteins determined can aid in understanding metabolism in organisms, for example microbial metabolism.

In some embodiments, the method can utilize mass spectrometry to read out the identity, quantity and/or activity of gene products. For example, a peptide barcode that can be detected along with reaction substrates and products, using mass spectrometry, can encode the identity of the gene products. The same peptide barcode or another peptide barcode can, in some embodiments, be used to quantify the gene products. For example, a gene product can be linked via two protease labile sites to produce two peptide barcodes. With the protease labile sites, after expression of the gene product, protease treatment can produce the gene product (e.g., an enzyme) and two peptide barcodes. In some embodiments, one peptide barcode can be a barcode that encodes the identity of the expressed gene product, and the second peptide barcode can be a conserved quantification peptide. As another example, a gene product can be linked via a protease labile site to one peptide barcode. With the protease labile site, after expression of the gene product, protease treatment can produce the gene product and one peptides barcode. The single peptide barcode can encode the identity of the expressed gene product. Furthermore, the single peptide barcode can be used for quantification.

A mixture comprising an enzyme, reaction substrates and products, and one or more peptide barcodes can be screened for activities against a range of substrates, cofactors and reaction conditions to discover the activities of the enzyme. In some embodiments, the resulting reaction products and peptide barcodes can be identified using mass spectrometry. Using an internal standard, the quantity of expressed gene product can be determined to estimate the specific activities of the gene product.

The systems and methods disclosed herein can enable combinatorial experimental designs, allowing for multiplexing and high throughput (e.g., ultrahigh throughput). Where spectrometry-based approaches may be hindered by low-throughput and a limited ability to multiplex, the systems and methods disclosed herein enable rapid discovery of the function of genes. In some embodiment, the method can be used in enzyme-related processes, such as biomanufacturing of enzymes and enzyme research. Thus, the method can be used for rapid discovery of the function of genes.

Determination of Gene Functions

Disclosed herein are methods for rapid and scalable discovery of gene functions. The methods can enable combinatorial experimental designs, which can in turn allow multiplexing and ultrahigh-throughput. FIG. 1 is a non-limiting exemplary schematic illustration of a method for enzyme identification according to the scope of the present disclosure. In some embodiments, the methods can utilize mass spectrometry to determine both the identities and activities of gene products such as proteins and enzymes. In some embodiments, the methods can utilize liquid handling (e.g., massively-parallel automatic liquid handling or robotic liquid handling), DNA synthesis, protein expression (e.g., recombinant protein production) and characterization, and/or computation analysis for determining the biochemical function of gene products or for genome mining. For example, mass spectrometry data can be segmented into well-regions (e.g., mass spectra belonging to different experiments, one experiment per well). As another example, automated sample analysis can be used to analyze experimental data such as mass spectra.

The methods, compositions, and systems disclosed herein can utilize mass spectrometry techniques, including enzyme activity profiling, (exo-) metabolomics and mass spectrometry imaging, to study metabolomics. In some embodiments, nanostructure-initiator mass spectrometry (NIMS) can be used in conjunction with nanoliter-scale manipulation of liquids for rapid mass spectrometry functional analysis. Using bioconjugate chemistry, highly versatile and sensitive substrates can be synthesized, thus enabling rapid detection and quantification using NIMS. Furthermore, microfluidic devices can be integrated with the NIMS technology, to further improve throughput and decrease reagent usage. In some embodiments, bioinformatic tools, for example OpenMSI and Metabolite Atlas, can be used to analyze mass spectrometry data In some embodiments, the methods can comprise providing a sample comprising a barcoded protein such as an enzyme, wherein the barcoded protein comprises the protein cleavably fused to a barcode (for example, a peptide barcode), and wherein the barcoded protein is produced by in vitro transcription and translation. FIG. 1 panels a-c show in vitro transcription and translation of three genes. The identities of the genes can be encoded using barcodes that can be detected along with reaction substrates and products using mass spectrometry. DNA synthesis can be used to generate genes fused via an enzyme cleavable site, for example a protease cleavage site, to the unique sequences for barcodes.

Barcodes, for example peptide barcodes, can be used to uniquely identify proteins. For example, a putative thiopurine methyl transferase can be cleavably fused to a peptide barcode with sequence GTFLRN (Seq ID No: 1), and a putative β-glucosidase can be cleavably fused to a peptide barcode with sequence QRWTFLLRN (Seq ID No: 2). After in vitro transcription and translation of these two proteins, the peptide barcode with sequence GTFLRN (Seq ID No: 1) can be cleaved off from the putative thiopurine methyl transferase, and the peptide barcode with sequence QRWTFLLRN (Seq ID No: 2) can be cleaved off from the putative β-glucosidase. The putative thiopurine methyl transferase can be incubated with a substrate (e.g., 6-mercaptopurine) and a cofactor (e.g., S-adenosyl-methionine (SAM)) of thiopurine methyl transferase in a reaction mixture. The putative β-glucosidase can be incubated with a substrate (e.g., a cellobiose) in another reaction mixture. Reaction mixtures can be analyzed by mass spectrometry, for example liquid chromatograph-electrospray ionization-mass spectrometry, to generate mass spectra.

The identity and the activity of proteins can be simultaneously determined by mass spectrometry. For example, if a mass spectrum contains ions corresponding to the peptide with sequence GTFLRN (Seq ID No: 1), the protein in the reaction mixture can be determined to be the putative thiopurine methyl transferase. And if the mass spectrum contains ions corresponding to methylated 6-mercaptopurine, the protein in the reaction mixture can be determined to be a thiopurine methyl transferase. As another example, if a mass spectrum contains ions corresponding to the peptide with sequence QRWTFLLRN (Seq ID No: 2), the protein in the reaction mixture can be determined to be the putative β-glucosidase. And if the mass spectrum contains ions corresponding to cleaved cellobiose, the protein in the reaction mixture can be determined to be a β-glucosidase. In some embodiments, mass spectra can be analyzed with computational tools to determine proteins of interest that can be further validated subsequently.

In FIG. 1 panel a, a "gene a" transcribed into an mRNA of the "gene a" (not shown) which in turn can be translated into a copy of the "protein A," for example an enzyme A. The "gene a" can be modified with a nucleotide sequence encoding a barcode. For example, the "gene a" can be fused to a first nucleotide sequence encoding a "barcode A". The transcription and translation of the modified "gene a" fused to the nucleotide sequence can produce a barcoded "protein A." The barcode region of the barcoded "protein A" is shown as a tail, for example a first tail, attached to the "protein A." In FIG. 1 panel b, a "gene b" can be transcribed into an mRNA of the "gene b" (not shown) which in turn can be translated into a copy of the "protein B," for example an enzyme B. The "gene b" can be modified with a nucleotide sequence encoding a barcode. For example, the "gene b" can be fused to a second nucleotide sequence encoding a "barcode B". The transcription and translation of the modified "gene b" can produce a barcoded "protein B." The barcode region of the barcoded "protein B" is shown as a tail, for example a second tail, attached to the "protein B." In FIG. 1 panel c, a "gene c" can be transcribed into an mRNA of the "gene c" (not shown) which in turn can be translated into a copy of the "protein C," for example an enzyme C. The "gene c" can be modified with a nucleotide sequence encoding a barcode. For example, the "gene c" can be fused to a third nucleotide sequence encoding a third barcode sequence. The transcription and translation of the modified "gene c" can produce a barcoded "protein C." The barcode region of the barcoded "protein C" is shown as a tail, for example a third tail, attached to the "protein C."

The nucleotide sequences encoding barcodes can vary. For example, the first nucleotide sequence, the second nucleotide sequence, and the third nucleotide sequence can be the same, thus coding the same barcode. For example, the three nucleotide sequences can be different, although they can code the same barcode. For example, the three nucleotide sequences can be different and code different barcodes.

In some embodiment, the methods can comprise incubating the barcoded protein with a protease capable of removing the barcode from the barcoded protein to generate a non-barcoded protein. FIG. 1 panels d-f show barcode cleavage. In FIG. 1 panel d, the barcode attached to the barcoded "protein A" can be cleaved off to generate a barcode and a non-barcoded "protein A." For example, the "barcode A" attached to the barcoded "protein A" can be cleaved off to generate a copy of the "barcode A" and a non-barcoded "protein A." In FIG. 1 panel e, the barcode attached to the barcoded "protein B" can be cleaved off to generate a barcode and a non-barcoded "protein B." For example, the "barcode B" attached to the barcoded "protein B" can be cleaved off to generate a copy of the "barcode B" and a non-barcoded "protein B." In FIG. 1 panel f, the barcode attached to the barcoded "protein C" can be cleaved off to generate a barcode and a non-barcoded "protein C." For example, the third barcode attached to the barcoded "protein C" can be cleaved off to generate a copy of the "barcode C" and a non-barcoded "protein C."

In some embodiments, the methods can comprise incubating the non-barcoded protein with a candidate substrate and a cofactor to obtain a modified candidate substrate. The modified candidate substrate can comprise the cofactor. In FIG. 1 panel g, the "protein A" can modify a candidate substrate to produce a modified candidate substrate. For example, the "protein A" can add a "cofactor C" to a candidate substrate S to produce a modified candidate substrate S-C. In FIG. 1 panel h, the "protein B" cannot modify a candidate substrate to produce a modified candidate substrate. For example, the "protein B" cannot add a "cofactor C" to a candidate substrate S to produce a modified candidate substrate S-C under the reaction condition. In FIG. 1 panel i, the "protein C" can modify a candidate substrate to produce a modified candidate substrate. For example, the "protein C" can add a "cofactor C" to a candidate substrate S to produce a modified candidate substrate S-C.

In some embodiments, the methods can comprise generating a mass spectrum. In some embodiments, the method can comprise: determining an activity of the protein with respect to the candidate substrate by identifying candidate substrate ions, modified candidate substrate ions, and/or cofactor ions based on the mass spectrum; and determining the identity of the barcoded enzyme in the sample by identifying barcode ions in the mass spectrum. Mass spectrometry can be used to generate mass spectra containing the candidate substrates, modified candidate substrates, and barcodes.

FIG. 1 panels j-l show mass spectrometry analysis. The mass spectrum of FIG. 1 panel j shows ions of the "barcode A" and the modified candidate substrate S-C. This mass spectrum shows the "barcode A" and the modified candidate substrate and can indicate that the candidate substrate is a substrate of the "protein A." The mass spectrum of FIG. 1 panel k shows ions of the "barcode B" and the candidate substrate S. This mass spectrum shows the "barcode B" and the candidate substrate and can indicate that the candidate substrate is not a substrate of the "protein B" under the reaction condition. The mass spectrum of FIG. 1 panel l shows ions of the "barcode B" and the modified candidate substrate S-C. This mass spectrum show the "barcode C" and the modified candidate substrate and can indicate that the candidate substrate is a substrate of the "protein C." Consequently, the methods disclosed herein can advantageously determine the identity and the activity of a gene product in one mass spectrum.

In some embodiments, the methods disclosed herein can advantageously enable the acquisition of experimental data about the function of an enzyme, the substrate specificity of an enzyme, and/or the cofactor specificity of an enzyme. In some embodiments, variants of an enzyme can be selected for analysis. For example, 300 combinations of glycosyl hydrolases (e.g., mutants of a glycosyl hydrolase) and substrates can be selected for analysis based on database mining of glycosyl hydrolase.

In some embodiments, the methods disclosed herein can advantageously allow inferring the regioselectivity of an enzyme and/or the stereoselectivity of an enzyme. In some embodiments, the methods disclosed herein can advantageously facilitate screening of variants of an enzyme for activity against a substrate(s), such as for directed evolution or metagenomic mining, and/or for activity against one or more cofactors, such as for directed evolution or metagenomic mining.

In some embodiments, the methods disclosed herein can be used for detecting a chemical in a mixture by monitoring its modification by an enzyme. In some embodiments, the methods disclosed herein can be used for testing DNAs designed to encode the multiple genes encoding a biosynthetic pathway, for testing chemical production of DNAs of natural origin, for testing chemical production on a plurality of DNAs, such as for combinatorial or directed evolution experiments, and/or for testing a plurality of DNAs to optimize the expression or function of a pathway using combinatorial or directed evolution experiments. In some embodiments, the methods disclosed herein can be used for monitoring the reactions of a purified enzyme and/or the reaction of an enzyme in a complex mixture.

Figure 2:
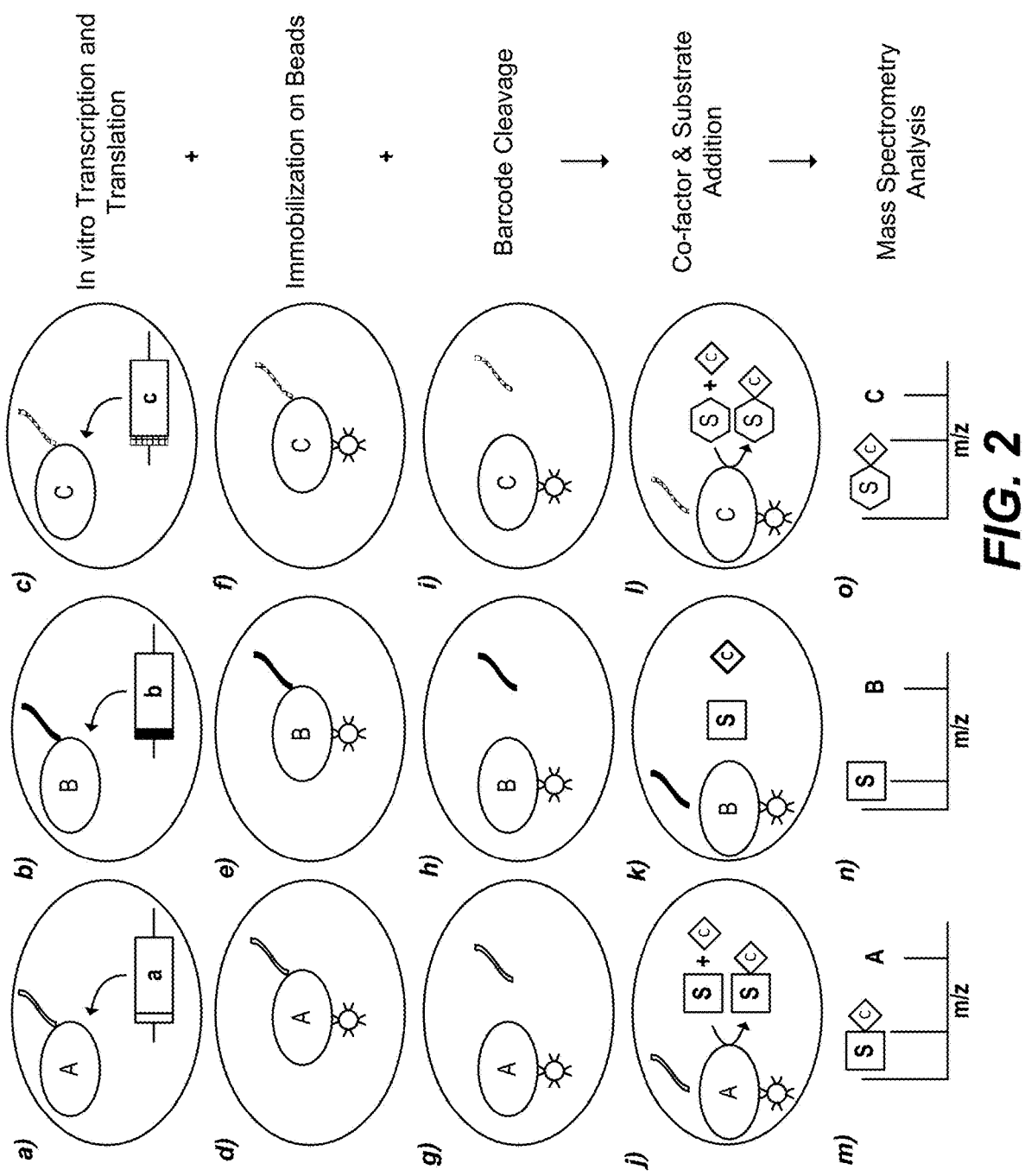
FIG. 2 is a non-limiting exemplary schematic illustration of a method for enzyme identification using beads according to the scope of the present disclosure.

Disclosed herein are methods for rapid and scalable discovery of gene functions. FIG. 2 is a non-limiting exemplary schematic illustration of a method for enzyme identification using beads according to the scope of the present disclosure. In some embodiments, the methods can comprise providing a sample comprising a barcoded protein such as an enzyme, wherein the barcoded protein comprises the protein cleavably fused to a barcode (for example, a peptide barcode), and wherein the barcoded protein is produced by in vitro transcription and translation. FIG. 2 panels a-c, similar to FIG. 1 panels a-c, show in vitro transcription and translation of three genes. Briefly, a "gene a" can be transcribed and translated into a copy of the "protein A." A "gene b" can be transcribed and translated into a copy of the "protein B." A "gene c" can be transcribed and translated into a copy of the "protein C."

In some embodiments, the methods can comprise immobilizing the barcoded protein on one or more synthetic particles, for example beads (e.g., magnetic beads), to generate an immobilized barcoded protein. FIG. 2 panels d-f show immobilization of proteins on beads, for example magnetic beads. For example, the "protein A" can be immobilized on a first synthetic particle to generate an immobilized "protein A". The "protein B" can be immobilized on a second synthetic particle to generate an immobilized "protein B." The "protein C" can be immobilized on a third synthetic particle to generate an immobilized "protein C." In some embodiments, the barcoded protein can be produced in vivo and purified by immobilization on beads, for example magnetic beads.

In some embodiment, the methods can comprise incubating the immobilized barcoded protein with a protease capable of removing the barcode from the barcoded protein to generate an immobilized non-barcoded protein. FIG. 2 panels g-i, similar to FIG. 1 panels d-f, show barcode cleavage. Briefly, the "barcode A" attached to the immobilized barcoded "protein A" can be cleaved off to generate a copy of the "barcode A" and an immobilized non-barcoded "protein A." The "barcode B" attached to the barcoded "protein B" can be cleaved off to generate a copy of the "barcode B" and an immobilized non-barcoded "protein B." The third barcode attached to the barcoded "protein C" can be cleaved off to generate a copy of the "barcode C" and an immobilized non-barcoded "protein C."

In some embodiments, the methods can comprise incubating the immobilized non-barcoded protein with a candidate substrate and a cofactor to obtain a modified candidate substrate. The modified candidate substrate can comprise the cofactor. FIG. 2 panels j-i, similar to FIG. 1 panels d-f, show cofactor addition. Briefly, the immobilized non-barcoded "protein A" can add a "cofactor C" to a candidate substrate S to produce a modified candidate substrate S-C. The immobilized non-barcoded "protein B" cannot add a "cofactor C" to a candidate substrate S to produce a modified candidate substrate S-C under the reaction condition. The immobilized non-barcoded "protein C" can add a "cofactor C" to a candidate substrate S to produce a modified candidate substrate S-C.

In some embodiments, the methods can comprise removing the immobilized non-barcoded protein prior to generating a mass spectrum. For example, the synthetic particle comprises a magnetic bead, and removing the immobilized non-barcoded protein can comprise magnetically removing the immobilized non-barcoded protein. For example, removing the immobilized non-barcoded protein can comprise removing the immobilized non-barcoded protein by centrifugation. For example, removing the immobilized non-barcoded protein can comprise removing the immobilized non-barcoded protein by gravity.

In some embodiments, the methods can comprise generating a mass spectrum. In some embodiments, the method can comprise: determining an activity of the protein with respect to the candidate substrate by identifying candidate substrate ions, modified candidate substrate ions, and/or cofactor ions based on the mass spectrum; and determining the identity of the barcoded enzyme in the sample by identifying barcode ions in the mass spectrum. Mass spectrometry can be used to generate mass spectra containing the candidate substrates, modified candidate substrates, and barcodes.

FIG. 2 panels m-o, similar to FIG. 1 panels j-l, show mass spectrometry analysis. Briefly, the mass spectrum of FIG. 2 panel j, by showing the "barcode A" and the modified candidate substrate S-C, can indicate that the candidate substrate is a substrate of the "protein A." The mass spectrum of FIG. 2 panel k, by showing the "barcode B" and the candidate substrate S, can indicate that the candidate substrate S is not a substrate of the "protein A" under the reaction condition. The mass spectrum of FIG. 2 panel l, by showing the "barcode C" and the modified candidate substrate S-C, can indicate that the candidate substrate S-C is a substrate of the "protein C." Consequently, the methods disclosed herein can advantageously determine the identity and the activity of a gene product in one mass spectrum after removing the gene product.

Determining Substrate Specificity

Disclosed herein includes methods for determining substrate specificity of an enzyme. In some embodiments, the methods can comprise providing a sample comprising a barcoded enzyme, wherein the barcoded enzyme comprises the enzyme cleavably fused to a barcode (e.g., a peptide barcode). FIG. 1 panels a-c schematically illustrate three exemplary barcoded enzymes each fused to one peptide barcode. The methods can comprise incubating the barcoded enzyme with a protease capable of removing the barcode from the barcoded enzyme. FIG. 1 panels d-f schematically illustrate removing the barcodes from three exemplary barcoded enzymes to generate three exemplary enzymes. The methods can comprise incubating the enzyme with one or more candidate substrates to obtain one or more modified candidate substrates in one or more reactions. The methods can comprise incubating the enzyme with one or more cofactors. FIG. 1 panels g-i schematically illustrate incubating three exemplary enzymes each with a candidate substrate and a cofactor. The methods can comprise generating a mass spectrum of each of the one or more reactions. FIG. 1 panels g-i schematically illustrate three mass spectra, one for each of the three exemplary enzymes.

In some embodiments, the methods can comprise determining a substrate specificity of the enzyme with respect to each of the one or more candidate substrates based on the mass spectrum. The number of candidate substrates can vary. For example, the number of candidate substrates can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, $10^9$, or a number or a range between any two of these values. For example, the number of candidate substrates can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, or $10^9$. The number of candidate substrates in a reaction can vary. For example, the number of candidate substrates in a reaction can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. For example, the number of candidate substrates in a reaction can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, or 1000.

In some embodiments, the methods can comprise determining the identity of the barcoded enzyme in the sample by identifying peptide barcode ions in the mass spectrum. In some embodiments, determining the substrate specificity of the enzyme with respect to each of the one or more candidate substrates can be based on whether ions of each of the one or more modified candidate substrates are in the mass spectrum. In some embodiments, determining the substrate specificity of the enzyme with respect to each of the one or more candidate substrates can be based on the ratio of ions of each of the one or more candidate substrates and ions of a corresponding modified candidate substrate in the mass spectrum.

Enzyme Quantification

Disclosed herein are systems and methods for determining gene function. For example, the systems and methods can be used for efficient and scalable determination of gene functions by quickly and reliably determining the functions of putative proteins (e.g., enzymes). In some embodiments, the methods and systems are used for assignment of the reactions of gene products in organisms. The functions of putative proteins determined can aid in understanding metabolism in organisms, for example microbial metabolism.

Figure 3:
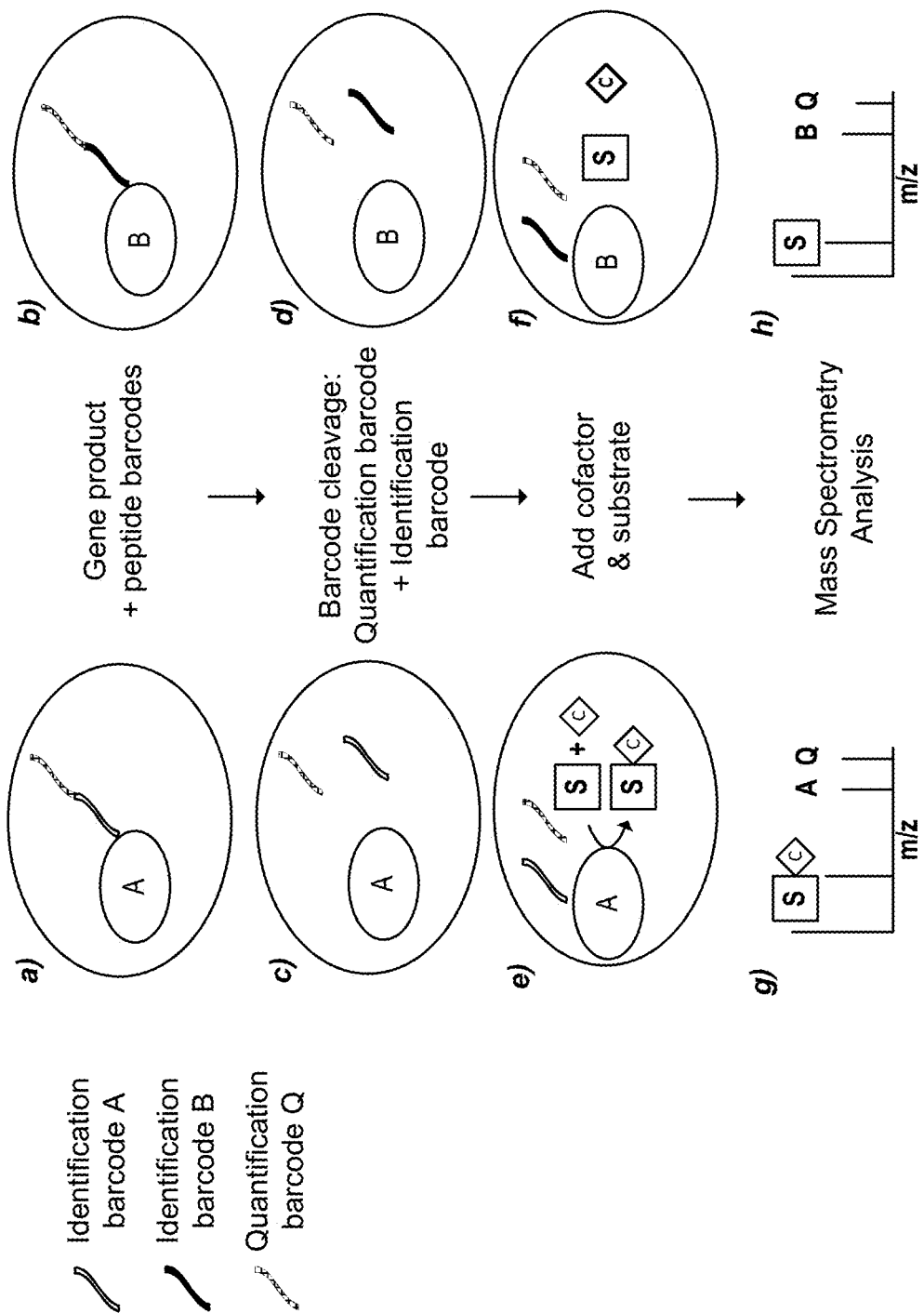
FIG. 3 shows a non-limiting exemplary schematic illustration of protein quantification for determining gene functions.

In some embodiments, the method can utilize mass spectrometry to read out the identity, quantity and/or activity of gene products. For example, a peptide barcode that can be detected along with reaction substrates and products, using mass spectrometry, can encode the identity of the gene products. The same peptide barcode or another peptide barcode can, in some embodiments, be used to quantify the gene products. For example, a gene product can be linked via two protease labile sites to produce two peptide barcodes. With the protease labile sites, after expression of the gene product (FIG. 3 panels a-b), protease treatment can produce the gene product (e.g., an enzyme) and two peptide barcodes. FIG. 3 panels c-d show that one peptide barcode can be a barcode that encodes the identity of the expressed gene product. For example, identification barcodes A and B can encode the identities of the expressed gene products, "protein A" and "protein B." Further, a second peptide barcode can be a quantification peptide that can similar or the same for the gene products. For example, a quantification barcode Q can be used for gene product quantification. By quantifying the amount of quantification peptide barcode present, the amount of soluble gene product can be determined because the molar ratio of the quantification peptide barcode and the gene product is 1:1.

FIG. 3 panel e, similar to FIG. 1 panel g and FIG. 2 panel j, shows that the "protein A" can modify a candidate substrate to produce a modified candidate substrate. For example, the "protein A" can add a "cofactor C" to a candidate substrate S to produce a modified candidate substrate S-C. FIG. 3 panel f, similar to FIG. 1 panel h and FIG. 2 panel k, shows that the "protein B" cannot modify a candidate substrate to produce a modified candidate substrate. For example, the "protein B" cannot add a "cofactor C" to a candidate substrate S to produce a modified candidate substrate S-C under the reaction condition.

Alternatively or in addition, a gene product can be linked via a protease labile site to one peptide barcode. With the protease labile site, after expression of the gene product, protease treatment can produce the gene product and one peptides barcode. The single peptide barcode can encode the identity of the expressed gene product. Furthermore, the single peptide barcode can be used for quantification.

A mixture comprising an enzyme, reaction substrates and products, and one or more peptide barcodes then can be screened for activities against a range of substrates, cofactors and reaction conditions to discover the activities of the enzyme. In some embodiments, the resulting reaction products and peptide barcodes can be identified using mass spectrometry. FIG. 3 panels g-h show mass spectrometry analysis. FIG. 3 panel g, similar to FIG. 1 panel j and FIG. 2 panel m, shows a mass spectrum with ions of the "barcode A" and the modified candidate substrate S-C. This mass spectrum shows the "barcode A" and the modified candidate substrate and can indicate that the candidate substrate is a substrate of the "protein A." The quantity of the "protein A" that catalyzes the addition of the cofactor to the substrate can be determined based on the quantity of the "barcode Q" in the mass spectrum. FIG. 3 panel h, similar to FIG. 1 panel k and FIG. 2 panel n, shows a mass spectrum with ions of the "barcode B" and the candidate substrate S. This mass spectrum shows the "barcode B" and the candidate substrate and can indicate that the candidate substrate is not a substrate of the "protein B" under the reaction condition. The quantity of the "protein B" in the reaction can be determined based on the quantity of the "barcode Q" in the mass spectrum. The relative quantities of the "protein A" and the "protein B" can be determined based the relative quantities of the "barcode Q" in the mass spectra shown in FIG. 3 panels g-h. In some embodiments, the quantities of expressed gene products can be determined using a standard of the "barcode Q." With the quantities of the express gene products, specific activities of the gene products can be estimated. Consequently, the methods disclosed herein can advantageously determine the identity, the quantity, and the activity of a gene product in one mass spectrum.

Identifying Enzymes Capable of Modifying Substrates of Interest

Disclosed herein are methods for identifying enzymes capable of modifying substrates of interest. In some embodiments, the methods can comprise: providing one or more barcoded enzymes, wherein each of the barcoded enzymes can be cleavably fused to a barcode (e.g., peptide barcode); incubating the one or more barcoded enzymes with a protease capable of removing the peptide barcode from the one or more barcoded enzymes and the substrate of interest to obtain a modified substrate of interest in one or more reactions; generating a mass spectrum of each of the one or more reactions; and determining the activity of each of the one or more barcoded enzymes with respect to the substrate of interest based on the mass spectrum. In some embodiments, the methods can comprise incubating the one or more barcoded enzymes with one or more cofactors. In some embodiments, the substrate of interest can be a candidate substrate.

In some embodiments, incubating the barcoded enzymes with the protease and the substrate of interest can comprise incubating two or more barcoded enzymes with the protease and the substrate of interest. The number of barcoded enzymes tested in a reaction can vary. In some embodiments, the number of barcoded enzymes tested in a reaction can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of barcoded enzymes tested in a reaction can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, or 1000.

In some embodiments, determining an activity of each of the one or more barcoded enzymes can be based on whether ions of the modified substrate of interest are in the mass spectrum. Determining the activity of each of the one or more barcoded enzymes can be based on the ratio of the substrate of interest ions and the modified substrate of interest ions in the mass spectrum.

Quantifying Enzymatic Activities

Disclosed herein are methods for quantifying enzymatic activities. In some embodiments, the methods can comprise: providing one or more barcoded enzymes, wherein each of the one or more barcoded enzymes can be cleavably fused to a first peptide barcode; for each of the one or more barcoded enzymes: incubating the barcoded enzyme with a protease capable of removing the peptide barcode from the barcoded enzyme and a candidate substrate to obtain a modified candidate substrate in a reaction; generating a mass spectrum of the reaction; quantifying the barcoded enzyme in the reaction based on the mass spectrum; and quantifying the enzymatic activity of the barcoded enzymes with respect to the candidate substrate based on the ratio of the candidate substrate and the modified candidate substrate in the mass spectrum. In some embodiments, the methods can comprise incubating the barcoded enzyme with one or more cofactors.

In some embodiments, quantifying the barcoded enzyme can be based on the first peptide barcode ions in the mass spectrum. In some embodiments, each of the barcoded enzymes can be further cleavably fused to a second peptide barcode. The protease can be capable of removing the second peptide barcode from each of the barcoded enzymes, or the protease may be unable to remove the second peptide barcode from each of the barcoded enzymes. Quantifying the barcoded enzyme can be based on the second peptide barcode ions in the mass spectrum. Quantifying the barcoded enzyme can be based on an internal standard of the second peptide barcode.

In some embodiments, quantifying the barcoded enzyme can be based on an internal standard, for example an isotopically labeled internal standard, of a barcode, for example the first peptide barcode or the second peptide barcode. In some embodiments, the first peptide barcode or the second peptide barcode can comprise amino acids with modified side chains; and quantifying the barcoded enzyme can be based on the amino acids with modified side chains using mass spectrometry or spectroscopy. In some embodiments, quantifying the barcoded enzyme can be based on peptide labeling, for example isobaric peptide labeling, or labeled synthetic peptides.

The sequences of the first peptide barcode and the second peptide barcode can vary. In some embodiments, the first peptide barcode and the second peptide barcode can be the same. In some embodiments, the first peptide barcode differ by or by about 1, 2, 3, 4, 5, 6, 7, 8, 9, 10, 11, 12, 13, 14, 15, 16, 17, 18, 19, 20, or a number or a range between any two of these values, amino acids. In some embodiments, the first peptide barcode differ by at least, or at most, 1, 2, 3, 4, 5, 6, 7, 8, 9, 10, 11, 12, 13, 14, 15, 16, 17, 18, 19, or 20, amino acids.

Metabolic Pathway

Disclosed herein includes methods for determining activities of a number of enzymes, for example determine the activities enzymes involved in the same metabolic pathway. In some embodiments, the methods can comprise: providing a first barcoded enzyme and a second non-barcoded enzyme, wherein the first barcoded enzyme is cleavably fused to a barcode (e.g., a peptide barcode); incubating the first barcoded enzyme and the second non-barcoded enzyme with a protease capable of removing the peptide barcode from the first barcoded enzyme and one or more candidate substrates to obtain one or more modified candidate substrates in one or more reactions; generating a mass spectrum of each of the one or more reactions; determining the activities of the first barcoded enzyme and the second non-barcoded enzyme with respect to each of the one or more candidate substrates based on the mass spectrum; and determining the identities of the barcoded enzyme and the second non-barcoded enzyme by identifying peptide barcode ions in the mass spectrum. In some embodiments, the methods comprise incubating the first barcoded enzyme and the second non-barcoded enzyme with one or more cofactors.

In some embodiments, the methods can comprise: providing a first barcoded enzyme and one or more second non-barcoded enzymes, wherein the first barcoded enzyme is cleavably fused to a barcode (e.g., a peptide barcode); incubating the first barcoded enzyme and the second non-barcoded enzymes with a protease capable of removing the peptide barcode from the first barcoded enzyme and one or more candidate substrates to obtain one or more modified candidate substrates in one or more reactions; generating a mass spectrum of each of the one or more reactions; determining the activities of the first barcoded enzyme and the second non-barcoded enzymes with respect to each of the one or more candidate substrates based on the mass spectrum; and determining the identities of the barcoded enzyme and the second non-barcoded enzymes by identifying peptide barcode ions in the mass spectrum.

The number of second non-barcoded enzymes can vary. In some embodiments, the number of second non-barcoded enzymes can be, or be about, 1, 2, 3, 4, 5, 6, 7, 8, 9, 10, 20, 30, 40, 50, 60, 70, 80, 90, 100, or a number or a range between any two of these values. In some embodiments, the number of second non-barcoded enzymes can be at least, or at most, 1, 2, 3, 4, 5, 6, 7, 8, 9, 10, 20, 30, 40, 50, 60, 70, 80, 90, or 100.

In some embodiments, there can be one second non-barcoded enzyme, and the barcode (e.g., a peptide barcode) can encode the identities of the first barcoded enzyme and the second non-barcoded enzyme. For example, an in vitro transcription/translation system can be used to transcribe and translate polycistronic messenger ribonucleic acids (mRNAs) that encode the first barcoded enzyme and the second non-barcoded enzyme. The first barcoded enzyme can be cleavably fused to a barcode such as a peptide barcode. The second non-barcoded enzyme may not be fused to any barcode. Because of transcription and translation of polycistronic mRNAs encoding both the first barcoded enzyme and the second non-barcoded enzyme, a reaction mixture can contain both the first barcoded enzyme and the second non-barcoded enzyme. Consequently, if a reaction mixture gives rise to a mass spectrum containing ions corresponding to the barcode, the first barcoded enzyme and the second non-barcoded enzyme can be determined to be present in the reaction mixture. Thus, the peptide barcode can encode the identity of the first barcoded enzyme and the identity of the second non-barcoded enzyme simultaneously even though only the first barcoded enzyme is cleavably fused to the peptide barcode. Because a peptide barcode sequence can encode a unique combination of enzymes, fewer barcodes may be necessary to identify all the enzymes. For example, to determine the activities of ten combinations of two different enzymes, ten peptide barcodes, not 20 peptide barcodes, may be required to encode the identities of the enzymes.

In some embodiments, the first barcoded enzyme and the second non-barcoded enzymes can be involved in the same metabolic pathway. In some embodiments, determining the activities of the first barcoded enzyme and the second non-barcoded enzymes with respect to each of the one or more candidate substrates can be based on whether ions of each of the one or more modified candidate substrates are in the mass spectrum. In some embodiments, determining the activities of the first barcoded enzyme and the second non-barcoded enzymes with respect to each of the one or more candidate substrates can be based on the ratio of ions of each of the one or more candidate substrates and ions of a corresponding modified candidate substrate in the mass spectrum.

In some embodiments, the first barcoded enzyme and the second non-barcoded enzymes can be incubated with the protease after or prior to being incubated with the one or more candidate substrates. In some embodiments, the first barcoded enzyme and the second non-barcoded enzymes can be incubated with the protease and the one or more candidate substrates simultaneously.

In some embodiments, providing the first barcoded enzyme and the second non-barcoded enzymes can comprises: providing a polynucleotide encoding the first barcoded enzyme and the second non-barcoded enzymes; and incubating the polynucleotide in a cell-free transcription/translation reaction to generate the first barcoded enzyme and the second non-barcoded enzyme. In some embodiments, providing the first barcoded enzyme and the second non-barcoded enzymes can comprise: providing a first polynucleotide encoding the first barcoded enzyme; providing a second polynucleotide encoding the second non-barcoded enzymes; and incubating the first polynucleotide and the second polynucleotide in a cell-free transcription/translation reaction to generate the first barcoded enzyme and the second non-barcoded enzyme. In some embodiments, providing the first barcoded enzyme and the second non-barcoded enzymes can comprise: providing a first polynucleotide encoding the first barcoded enzyme; for each of the second non-barcoded enzymes, providing a second polynucleotide encoding the second non-barcoded enzyme; and incubating the first polynucleotide and the second polynucleotides in a cell-free transcription/translation reaction to generate the first barcoded enzyme and the second non-barcoded enzyme. In some embodiments, providing the first barcoded enzyme and the second non-barcoded enzymes can comprise: providing a first polynucleotide encoding the first barcoded enzyme; for some of the second non-barcoded enzymes, providing a second polynucleotide encoding some of the second non-barcoded enzymes; and incubating the first polynucleotide and the second polynucleotide in a cell-free transcription/translation reaction to generate the first barcoded enzyme and the second non-barcoded enzyme. In some embodiments, the first barcoded enzyme and the second non-barcoded enzyme were produced together in a cell-based expression system, for example an *E. coli* expression system.

The number of second non-barcoded enzymes encoded by a second polynucleotide can vary. In some embodiments, a second polynucleotide can encode or can encode about 1, 2, 3, 4, 5, 6, 7, 8, 9, 10, 20, 30, 40, 50, 60, 70, 80, 90, 100, or a number or a range between any two of these values, enzymes. In some embodiments, a second polynucleotide can encode at least, or at most, 1, 2, 3, 4, 5, 6, 7, 8, 9, 10, 20, 30, 40, 50, 60, 70, 80, 90, or 100, enzymes. The number of second polynucleotides can vary. In some embodiments, there can be, or be about, 1, 2, 3, 4, 5, 6, 7, 8, 9, 10, 20, 30, 40, 50, 60, 70, 80, 90, 100, or a number or a range between any two of these values, second polynucleotides. In some embodiments, there can be at least, or at most, 1, 2, 3, 4, 5, 6, 7, 8, 9, 10, 20, 30, 40, 50, 60, 70, 80, 90, or 100, second polynucleotides.

Multiplexing

The methods, compositions, and systems disclosed herein can have multiplex capability for determining substrate specificity, enzymes capable of modifying substrates of interest, quantifying enzymatic activities, and/or determining activities of a number of enzymes in a metabolic pathway. In some embodiments, the methods can be multiplexed. The number of multiplexed reactions can vary, for example, ranging from 1 to $10^9$. For example, the number of multiplexed reactions can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, $10^9$, or a number or a range between any two of these values. For example, the number of multiplexed reactions can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, or $10^9$.

Barcodes and Barcode Cleavage

The number of peptide barcodes fused to a barcoded enzyme can vary, for example, ranging from 1 to 100. In some embodiments, the number of peptide barcodes fused to a barcoded enzyme can be, or be about, 1, 2, 3, 4, 5, 6, 7, 8, 9, 10, 20, 30, 40, 50, 60, 70, 80, 90, 100, or a number or a range between any two of these values. In some embodiments, the number of peptide barcodes fused to the barcoded enzyme can be at least or can be at most 1, 2, 3, 4, 5, 6, 7, 8, 9, 10, 20, 30, 40, 50, 60, 70, 80, 90, or 100.

The location of a peptide barcode can vary. In some embodiments, a peptide barcode can be at or can be close to the N-terminus of a barcoded enzyme. In some embodiments, a peptide barcode can be or can be close to the C-terminus of a barcoded enzyme. In some embodiments, a peptide barcode can be at neither the N-terminus nor the C-terminus of a barcoded enzyme.

The number and the sequences of peptide barcodes can vary. In some embodiments, the number of peptide barcode sequences can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, $10^9$, or a number or a range between any two of these values. In some embodiments, the number of peptide barcode sequences can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, or $10^9$. In some embodiments, a peptide barcode can comprise the sequence of any one of SEQ ID No: 1-104 or any combination thereof.

TABLE 1

Peptide Barcode Sequences.

| Barcode amino acid sequence | Seq ID No: | Barcode amino acid sequence | Seq ID No: | Barcode amino acid sequence | Seq ID No: |
|---|---|---|---|---|---|
| GTFLRN | 1 | QTFLRNP | 36 | QTFLLRNM | 71 |
| QRWTFLLRN | 2 | QTFLRNV | 37 | NTFLLRNF | 72 |
| QTFLRN | 3 | QTFLRNT | 38 | QTFLLRNH | 73 |
| GTFLRNS | 4 | QTFLRNL | 39 | NTFLLRNR | 74 |
| GTFLLRNL | 5 | QTFLRNN | 40 | QTFLLRNF | 75 |
| NWTFLRN | 6 | GWTFLRN | 41 | NTFLLRNY | 76 |
| GTFLLRNH | 7 | NTFLRNM | 42 | QTFLLRNY | 77 |
| GTFLLRNF | 8 | NTFLRNH | 43 | NWTFLLRN | 78 |
| QTFLLRNI | 9 | QTFLRNK | 44 | GRTFLLRNV | 79 |
| NTFLLRNH | 10 | GTFLLRNS | 45 | GRTFLLRNI | 80 |
| QTFLLRNK | 11 | QTFLRNM | 46 | QRTFLLRNG | 81 |

TABLE 1-continued

Peptide Barcode Sequences.

| Barcode amino acid sequence | Seq ID No: | Barcode amino acid sequence | Seq ID No: | Barcode amino acid sequence | Seq ID No: |
|---|---|---|---|---|---|
| QRTFLLRN | 12 | NTFLRNF | 47 | GRTFLLRNM | 82 |
| GRTFLLRNP | 13 | QTFLRNH | 48 | GRTFLLRNH | 83 |
| QWTFLLRN | 14 | GTFLRNP | 49 | NRTFLLRNS | 84 |
| NRTFLLRNG | 15 | GTFLRNV | 50 | GRTFLLRNF | 85 |
| QRTFLLRNA | 16 | NTFLRNR | 51 | NRTFLLRNP | 86 |
| QRTFLLRNI | 17 | GTFLRNT | 52 | GRTFLLRNR | 87 |
| QRTFLLRNN | 18 | QTFLRNF | 53 | QRTFLLRNS | 88 |
| NRTFLLRNR | 19 | NTFLRNY | 54 | GRTFLLRNY | 89 |
| NTFLRN | 20 | QTFLRNR | 55 | QRTFLLRNP | 90 |
| GTFLRNP | 21 | QTFLRNY | 56 | QRTFLLRNV | 91 |
| GTFLRNV | 22 | QTFLLRNG | 57 | QRTFLLRNT | 92 |
| GTFLRNT | 23 | GTFLRNM | 58 | GRWTFLLRN | 93 |
| GTFLRNL | 24 | QTFLLRNA | 59 | NRTFLLRNM | 94 |
| NTFLRNG | 25 | QWTFLRN | 60 | NRTFLLRNH | 95 |
| QTFLRNG | 26 | NTFLLRNP | 61 | QRTFLLRNK | 96 |
| GTFLRNM | 27 | GTFLLRNR | 62 | QRTFLLRNM | 97 |
| GTFLRNH | 28 | QTFLLRNS | 63 | NRTFLLRNF | 98 |
| QTFLRNA | 29 | GTFLLRNY | 64 | QRTFLLRNH | 99 |
| NTFLRNS | 30 | QTFLLRNP | 65 | QRTFLLRNF | 100 |
| GTFLRNF | 31 | QTFLLRNV | 66 | NRTFLLRNY | 101 |
| NTFLRNP | 32 | QTFLLRNT | 67 | QRTFLLRNR | 102 |
| GTFLRNR | 33 | QTFLLRNN | 68 | QRTFLLRNY | 103 |
| QTFLRNS | 34 | GWTFLLRN | 69 | NRWTFLLRN | 104 |
| GTFLRNY | 35 | NTFLLRNM | 70 | | |

The length of a peptide barcode can vary, ranging from 3 to 50 amino acids. In some embodiments, the length of a peptide barcode can be, or be about, 3, 4, 5, 6, 7, 8, 9, 10, 20, 30, 40, 50, or a number or a range between any two of these values, amino acids in length. In some embodiments, the length of a peptide barcode can be at least or at most 3, 4, 5, 6, 7, 8, 9, 10, 20, 30, 40, or 50 amino acids in length.

In some embodiments, incubating the barcoded enzyme with the protease can comprise adding the barcoded enzyme into a solution, wherein the solution comprises the protease and the one or more candidate substrates. The protease can be WELQut protease (Thermo Fisher Scientific, Waltham, Mass.), Tobacco Etch Virus nuclear-inclusion-a endopeptidase (TEV protease), Enterokinase (EKT), Factor Xa protease, Thrombin, Rhinovirus (HRV) 3C Protease, or any combination thereof. In some embodiments, the peptide barcode can comprise the recognition sequence of the protease. The recognition sequence of the protease can be WELQ (Seq ID No: 105), ENLYFQ/G (Seq ID No: 106), DDDDK (Seq ID No: 107), IEGR (Seq ID No: 108), LVPRGS (Seq ID No: 109), LEVLFQGP (Seq ID No: 110), or any combination thereof.

Sample Incubation

The methods, compositions, and systems disclosed herein can be used to incubate a barcoded enzyme with one or more candidate substrates in one or more reactions. In some embodiments, the barcoded enzyme can be incubated with some or all of the one or more candidate substrates in one of the one or more reactions. In some embodiments, the barcoded enzyme can be incubated with one of the one or more candidate substrates in one of the one or more reactions. The number of candidate substrate in a reaction can vary. For example, the number of candidate substrates in a reaction can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, $10^9$, or a number or a range between any two of these values. For example, the number of candidate substrates in a reaction can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, or $10^9$.

The timing of incubating a barcoded enzyme with a protease capable of removing a peptide barcode from the barcoded enzyme and a candidate substrate or one or more candidate substrates can vary. In some embodiments, the barcoded enzyme can be incubated with the protease prior to being incubated with the candidate substrate or the one or more candidate substrates. In some embodiments, the barcoded enzyme can be incubated with the protease after being incubated with the candidate substrate or the one or more candidate substrates. In some embodiments, the barcoded enzyme can be incubated with the protease and the candidate substrate or the one or more candidate substrates simultaneously or close in time.

Barcoded enzymes can be incubated with a substrate of interest in one or more reactions. In some embodiments, some or all of the barcoded enzymes can be incubated with the substrate of interest in one of the one or more reactions. In some embodiments, one of the one or more barcoded enzymes can be incubated with the substrate of interest in one of the one or more reactions.

In some embodiments, incubating the one or more barcoded enzymes with the protease and the substrate of interest can comprise adding the barcoded enzymes into a solution, wherein the solution comprises the protease and the substrate of interest. The timing of incubating a barcoded enzyme with a protease capable of removing a peptide barcode, for example the first peptide barcode, and a substrate of interest can vary. The one or more barcoded enzymes can be incubated with the protease the substrate of interest simultaneously or close in time. The one or more barcoded enzymes can be incubated with the protease prior to being incubated with the substrate of interest. The one or more barcoded enzymes can be incubated with the protease after being incubated with the substrate of interest.

Reaction Volumes

The methods, compositions, and systems disclosed herein can be used to incubate a barcoded enzyme in one or more reactions. The reaction volumes can vary. In some embodiments, the volume of one reaction or the volume of at least one reaction can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, picoliters. In some embodiments, the volume of one reaction or the volume of at least one reaction can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, or 1000, picoliters. In some embodiments, the volume of a reaction or the volume of at least one reaction can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, nanoliters. In some embodiments, the volume of a reaction or the volume of at least one reaction can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, or 1000, nanoliters. In some embodiments, the volume of a reaction or the volume of at least one reaction can be, or be about, 1, 2, 3, 4, 5, 6, 7, 8, 9, 10, or a number or a range between any two of these values, microliters. In some embodiments, the volume of a reaction can be at least or can be at most 1, 2, 3, 4, 5, 6, 7, 8, 9, or 10, microliters.

The methods, compositions, and systems disclosed herein can comprise incubating or be used to incubate a barcoded enzyme in one or more reactions in microwells of a microwell array, for example a microtiter plate. A microwell array can comprise microwells of varying densities, for example ranging from 100 microwells per $inch^2$ to 10000 microwells per $inch^2$. In some embodiments, the number of microwells in a microwell array can be, or be about, 100, 200, 300, 400, 500, 600, 700, 800, 900, 1000, 2000, 3000, 4000, 5000, 6000, 7000, 8000, 9000, 10000, 20000, 30000, 40000, 50000, or a number or a range between any two of these values, microwells per $inch^2$. In some embodiments, the number of microwells in a microwell array can be at least or can be at most 100, 200, 300, 400, 500, 600, 700, 800, 900, 1000, 2000, 3000, 4000, 5000, 6000, 7000, 8000, 9000, 10000, 20000, 30000, 40000, or 50000, microwells per $inch^2$. In some embodiments, the number of microwells in a microwell array can be, or be about, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values, microwells per $cm^2$. In some embodiments, the number of microwells in a microwell array can be at least or can be at most 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 microwells per $cm^2$.

The total number of wells in a microwell array can vary based on the pattern and the spacing of the wells and the overall dimensions of the array. The number of microwells in the array can vary, for example, ranging from about 96 to about 1000000. In some embodiments, the number of microwells in the microarray can be, or be about, 96, 384, 1536, 2000, 3000, 4000, 5000, 6000, 7000, 8000, 9000, 10000, 20000, 30000, 40000, 50000, 60000, 70000, 80000, 90000, 100000, or a number or a range between any two of these values. In some embodiments, the number of microwells in the microarray can be at least or can be at most 96, 384, 1536, 2000, 3000, 4000, 5000, 6000, 7000, 8000, 9000, 10000, 20000, 30000, 40000, 50000, 60000, 70000, 80000, 90000, or 100000. In some embodiments, the number of microwells in the microwell array can be about 96. In some embodiments, the number of microwells can be about 150000.

Figure 4:
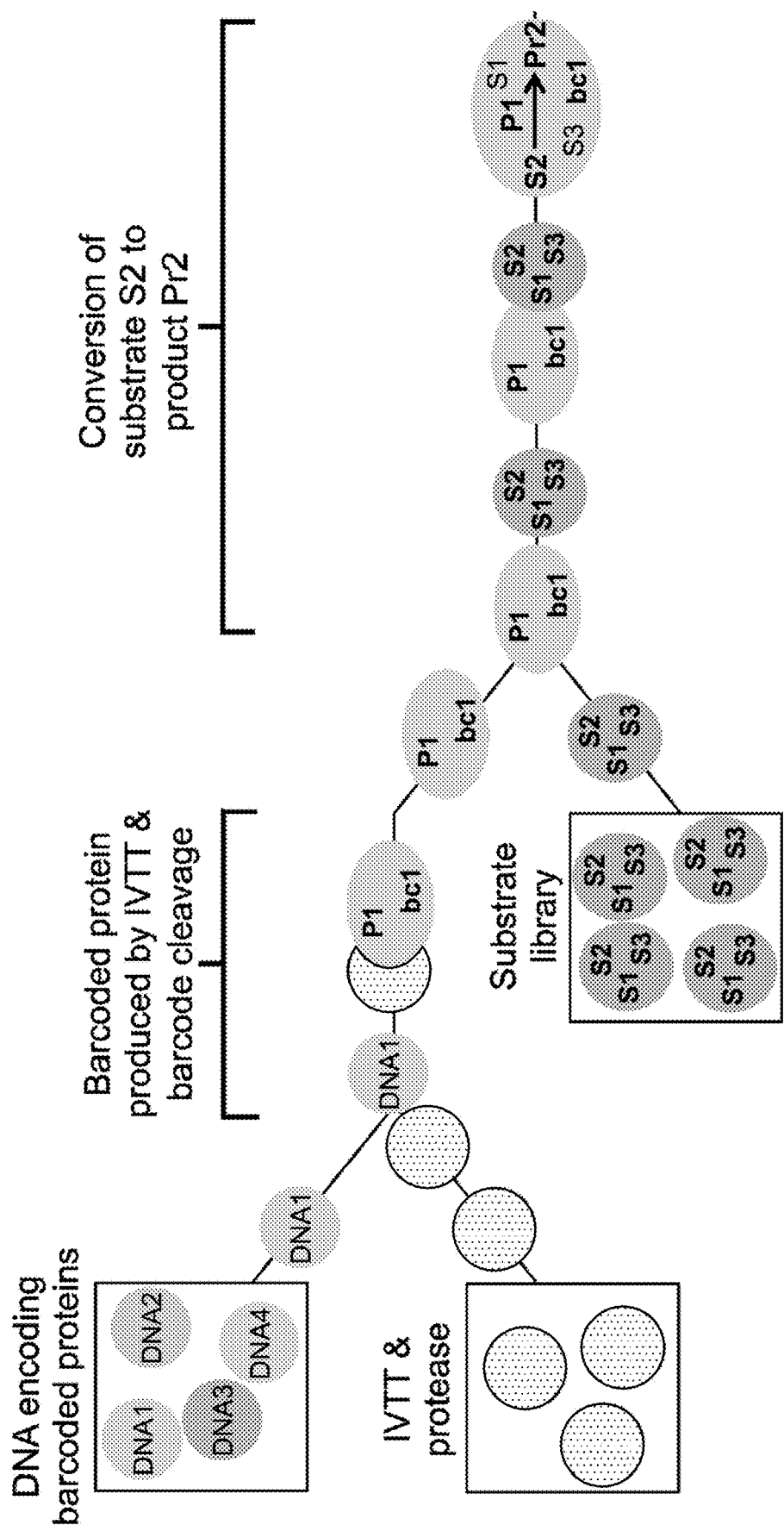
FIG. 4 shows a non-limiting exemplary schematic illustration of protein generation and identification using droplets.

In some embodiments, the methods, compositions, and systems disclosed herein can comprise incubating or be used to incubate a barcoded enzyme in one or more reactions in, for example, droplets generated using microfluidic devices. Microfluidic devices can allow for reliably manipulation of samples with small volumes (e.g., pL or nL) and performance at high throughputs (e.g., ultrahigh throughput). In one strategy, barcoded proteins can be produced inside droplets using a cell-free transcription/translation system or an in vitro transcription/translation system (FIG. 4). FIG. 4 shows a non-limiting exemplary schematic illustration of protein generation and identification using droplets. Linear dsDNA (e.g., DNA1-DNA4) encoding barcoded proteins and a cell-free transcription/translation system supplemented with a protease can be encapsulated into droplets (e.g., pl-nl droplets). After merging droplets containing dsDNA and droplets containing components of the cell-free transcription/translation system with a protease, the droplets can be incubated to produce the barcoded proteins (e.g., P1) cleaved barcodes (e.g., bc1).

Next, the barcode and the protein can be merged with a droplet containing (potential) substrates (e.g., S1, S2, S3), cofactors, other supplements, or any combination thereof. Modified and non-modified substrates, the quantification barcodes, the identification barcodes, or any combination thereof can be detected using mass spectrometry. For example, for functional pairings, a substrate "S2" can be modified and the modified substrate "Pr2" can be detected using MS.

Figure 5:
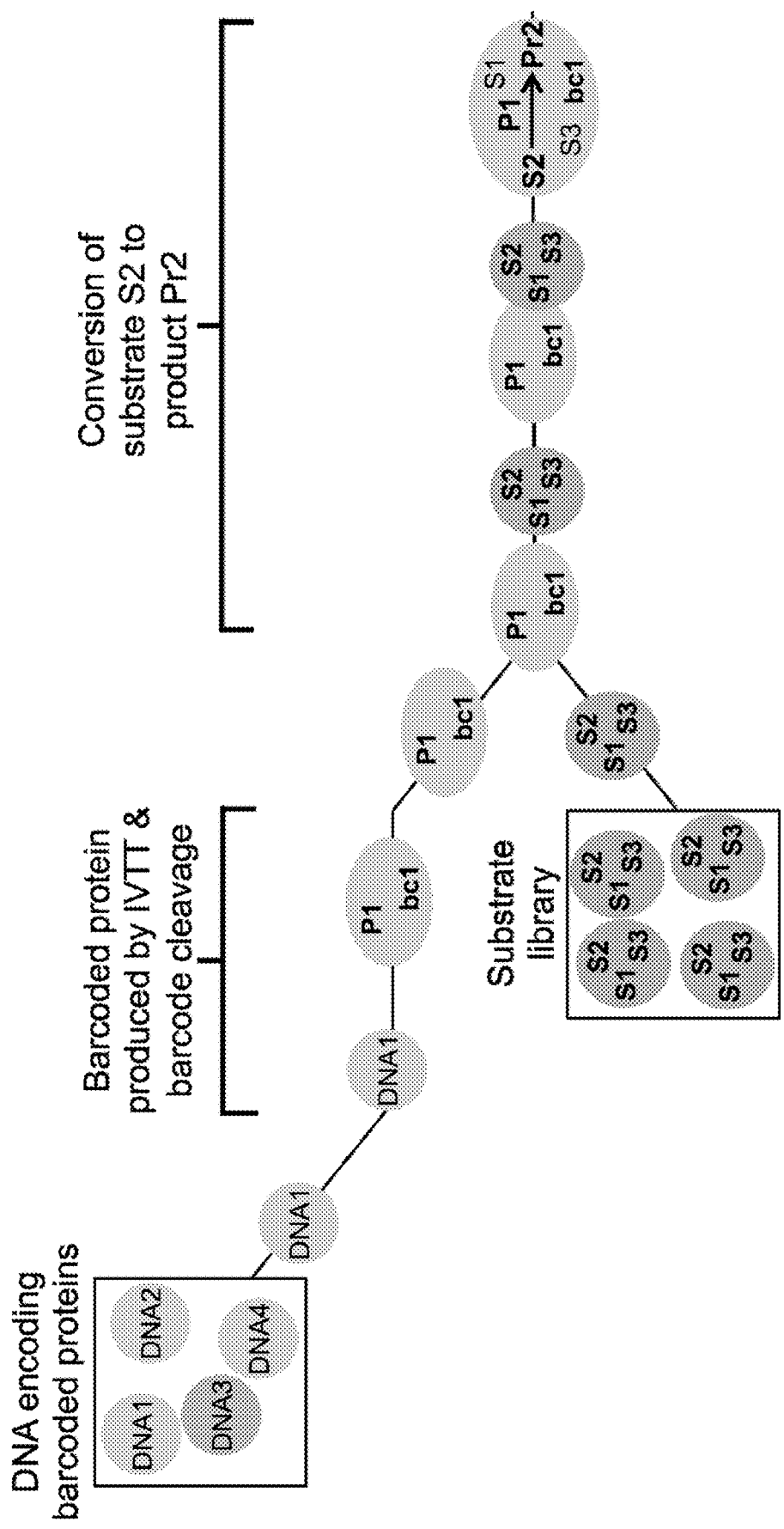
FIG. 5 shows a non-limiting exemplary schematic illustration of protein identification using droplets.

In a second strategy, purified barcoded proteins can be capsulated into droplets (FIG. 5). FIG. 5 shows a non-limiting exemplary schematic illustration of enzyme identification using droplets. Modified and non-modified substrates, the quantification barcodes, the identification barcodes, or any combination thereof can be detected using mass spectrometry. Barcoded proteins supplemented with a protease can be encapsulated into droplets (e.g., pl-nl droplets). Alternatively or in addition, droplets containing barcoded proteins and a protease can be merged. Barcode cleavage by the protease can occur in the droplets. Next, the barcode and the protein can be merged with a droplet containing (potential) substrates (e.g., S1, S2, S3), cofactors, other supplements, or any combination thereof. For example, for functional pairings, a substrate (S2) can be modified, and the modified substrate (Pr2) can be detected using MS.

In some embodiments, the reactions can occur in droplets. The number of droplets can be different in different implementations. In some embodiments, the number of droplets can be, or be about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values. In some embodiments, the number of droplets can be at least or can be at most 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000. Each droplet can include a nucleotide encoding a protein and one or more barcode sequences, components of a cell-free transcription/translation system, a barcoded protein, one or more (potential) substrates, one or more (potential) cofactors, one or more (potential) supplements, or any combination thereof.

The number of (potential) substrates, (potential) cofactors, and (potential) other supplements in a droplet can be different in different implementations. In some embodiments, the number of (potential) substrates, (potential) cofactors, and (potential) other supplements in a droplet can be, or about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, $10^9$, or a number or a range between any two of these values. In some embodiments, the number of (potential) substrates, cofactors, and other supplements in a droplet can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^7$, $10^8$, or $10^9$.

Cell Free Transcription/Translation

The methods, compositions, and systems disclosed herein can be used to determine an enzyme's substrate specificity, to determine whether an enzyme is capable of catalyzing a substrate of interest, or to quantify enzymatic activities. In some embodiments, the methods can comprise providing a barcoded enzyme. Providing a barcoded enzyme can comprise producing the barcoded enzyme using a cell-free transcription/translation system or an in vitro transcription/translation system. Non-limiting examples of cell-free transcription/translation systems include New England Biolabs, Inc. (Ipswich, Mass.) PURExpress® In Vitro Protein Synthesis Kit, Promega Corporation (Fitchburg, Wis.) TNT® Quick Coupled Transcription/Translation System, Clontech Laboratories (Mountain View, Calif.) Human Cell-Free Protein Expression System, and CellFree Sciences Co., Ltd. (Ehime, Japan) Protein Research Kit (S) from. In some embodiments, components of the cell-free transcription/translation system comprise a reaction buffer, a RNA polymerase, nucleotide triphosphates (NTPs), a ribonuclease inhibitor, a ribosome, aminoacyl-tRNA synthetase, tRNA, an amino acid mixture, an initiation factor, an elongation factor, a release factor, or a combination thereof.

In some embodiments, providing the sample comprising the barcoded enzyme comprises: providing a polynucleotide encoding the barcoded enzyme; and incubating the polynucleotide in a cell-free transcription/translation reaction to generate the barcoded enzyme. In some embodiments, providing the one or more barcoded enzymes comprises: providing polynucleotides each encoding one of the one or more barcoded enzymes; and incubating the polynucleotides in a cell-free transcription/translation reaction to generate the one or more barcoded enzymes. In some embodiments, providing the one or more barcoded enzymes comprises: for each of the one or more barcoded enzymes: generating a polynucleotide encoding the barcoded enzyme; and incubating the polynucleotide in a cell-free transcription/translation reaction.

E. coli Enzyme Production

The methods, compositions, and systems disclosed herein can be used to determine an enzyme's substrate specificity, to determine whether an enzyme is capable of catalyzing a substrate of interest, or to quantify enzymatic activities. In some embodiments, the methods can comprise providing a barcoded enzyme. Providing a barcoded enzyme can comprise producing the barcoded enzyme in a cell-based expression system such as a bacteria-based expression system (e.g., *E. coli*, or *B. subtilis*), a yeast-based expression system (e.g., *S. cerevisiae*) or an eukaryotic cell line-based expression system.

Mass Spectrometry

The methods, compositions, and systems disclosed herein can utilize mass spectrometry to generate a mass spectrum for each reaction after incubating an enzyme with a candidate substrate or a substrate of interest. In some embodiments, the mass spectrum can be generated using soft ionization mass spectrometry (MS), such as matrix associated laser desorption ionization (MALDI-MS) and nanostructure-initiator MS (NIMS). In some embodiments, the mass spectrum can be generated using electrospray ionization MS (ESI-MS), liquid chromatography ESI-MS, nanostructure-initiator MS (NIMS), fast atom bombardment MS, chemical ionization MS, atmospheric-pressure chemical ionization MS, matrix-assisted laser desorption/ionization MS, or any combination thereof.

In some embodiments, NIMS can be 100 or 1000 times faster and requires, for example, only 100th or 1000th of the volume needed for liquid chromatography-mass spectrometry. In some embodiments, NIMS can be used to increase the throughput and decrease the reagent costs. In some embodiments, substrates can be printed by, for example, acoustic printing for use with the NIMS technology. In some embodiments, substrate libraries can be selected and optimal assay conditions determined using NIMS.

Substrates and Modified Substrates

The methods, compositions, and systems disclosed herein can utilize different substrates of interest to produce varying modified candidate substrates. In some embodiments, a candidate substrate can be, or comprise, a protein, a peptide, a D- or L-amino acid, a nucleic acid, a nucleotide, a nucleoside, a sugar, a primary or secondary alcohol, an aldehyde, a ketone, a catechol, a metal ion, a quinone, or a combination thereof. In some embodiments, a candidate substrate can be, or comprise, 6-mercaptopurine, cellobiose, cellotetraose, xylotetraose, isoprimeverose, β-D-gentiobiose, xyloglucan and mannotriose, or any combination thereof. In some embodiments, the one or more candidate substrate can be agarose, amino acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof.

Candidate substrates can differ from one another. In some embodiments, candidate substrates can differ from one another by at least one functional group. The at least one functional group can be alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, or borinate. In some embodiments, candidate substrates can differ from one another by or by about 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, Daltons. In some embodiments, candidate substrates can differ from one another by at least or by at most 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, Daltons.

Candidate substrates and modified candidate substrates can have different structures and molecular weights. A substrate of interest and a modified substrate of interest can have different structures and molecular weights. In some embodiments, a candidate substrate or a substrate of interest can differ from its corresponding modified substrate by at least one functional group. In some embodiments, a candidate substrate or a substrate of interest can differ from its corresponding modified substrate by or by about 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, Daltons. In some embodiments, a candidate substrate can differ from its corresponding candidate modified candidate by at least or by at most 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, Daltons.

The number of candidate or potential substrates tested can differ. In some embodiments, the number of candidate substrates tested (e.g., in one or more droplets or microwells or a microwell array) can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, $10^9$, or a number or a range between any two of these values. In some embodiments, the number of candidate or potential substrates tested can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, or $10^9$.

Enzymes

The methods, compositions, and systems disclosed herein can be used to test different enzymes. In some embodiments, the enzymes can be, or can include, Enzyme Commission (EC) 1 oxidoreductases (e.g., a dehydrogenase or an oxidase); EC 2 transferases (e.g., a transaminase or a kinase); EC 3 Hydrolases (e.g., a lipase, an amylase, or a peptidase); EC 4 Lyases (e.g., a decarboxylase); EC 5 Isomerases (e.g., an isomerase or a mutase); or EC 6 Ligases (e.g., a synthetase).

In some embodiments, the enzymes can be, or can include, EC 1.1 oxidoreductases acting on the CH—OH group of donors; EC 1.2 oxidoreductases acting on the aldehyde or oxo group of donors; EC 1.3 oxidoreductases acting on the CH—CH group of donors; EC 1.4 oxidoreductases acting on the CH—NH(2) group of donors; EC 1.5 oxidoreductases acting on the CH—NH group of donors; EC 1.6 oxidoreductases acting on NADH or NADPH; EC 1.7 oxidoreductases acting on other nitrogenous compounds as donors; EC 1.8 oxidoreductases acting on a sulfur group of donors; EC 1.9 oxidoreductases acting on a heme group of donors; EC 1.10 oxidoreductases acting on diphenols and related substances as donors; EC 1.16 oxidoreductases oxidizing metal ions; EC 1.17 oxidoreductases acting on CH or CH(2) groups; EC 1.18 oxidoreductases acting on iron-sulfur proteins as donors; EC 1.19 oxidoreductases acting on reduced flavodoxin as donor; EC 1.20 oxidoreductases acting on phosphorus or arsenic in donors; EC 1.21 oxidoreductases catalyzing the reaction X-H+Y-H='X-Y'; EC 1.22 oxidoreductases acting on halogen in donors; EC 1.23 oxidoreductases reducing C—O—C group as acceptor; or EC 1.97 other oxidoreductases.

In some embodiments, the enzymes can be, or can include, EC 2.1 transferases transferring one-carbon groups with substrates: DNA, RNA, catechol; EC 2.2 transferases transferring aldehyde or ketonic groups; EC 2.3 acyltransferases; EC 2.4 glycosyltransferases; EC 2.5 transferases transferring alkyl or aryl groups, other than methyl groups; EC 2.6 transferases transferring nitrogenous groups; EC 2.7 transferases transferring phosphorus-containing groups; EC 2.8 transferases transferring sulfur-containing groups; EC 2.9 transferases transferring selenium-containing groups; or EC 2.10 transferases transferring molybdenum- or tungsten-containing groups.

In some embodiments, the enzymes can be, or can include, EC 3.1 hydrolases acting on ester bonds; EC 3.2 glycosylases; EC 3.3 hydrolases acting on ether bonds; EC 3.4 hydrolases acting on peptide bonds (peptidases); EC 3.5 hydrolases acting on carbon-nitrogen bonds, other than peptide bonds; EC 3.6 hydrolases acting on acid anhydrides; EC 3.7 hydrolases acting on carbon-carbon bonds; EC 3.8 hydrolases acting on halide bonds; EC 3.9 hydrolases acting on phosphorus-nitrogen bonds; EC 3.10 hydrolases acting on sulfur-nitrogen bonds; EC 3.11 hydrolases acting on carbon-phosphorus bonds; EC 3.12 hydrolases acting on sulfur-sulfur bonds; or EC 3.13 hydrolases acting on carbon-sulfur bonds.

In some embodiments, the enzymes can be, or can include, glycosyl hydrolases (enzymes that are useful for breaking down plant biomass for the production of biofuels), aminotransferases (proteins that are involved in binding and transport of small organic molecules or proteins that are important for biomanufacturing), solute binding proteins of ATP-binding cassette (ABC) transporter proteins (proteins involved in the metabolism of soil microbes with a potential impact in bioremediation), or any combination thereof.

In some embodiments, the enzymes can be, or can include, EC 4.1 carbon-carbon lyases; EC 4.2 carbon-oxygen lyases; EC 4.3 carbon-nitrogen lyases; EC 4.4 carbon-sulfur lyases; EC 4.5 carbon-halide lyases; EC 4.6 phosphorus-oxygen lyases; EC 4.7 carbon-phosphorus lyases; or EC 4.99 other lyases.

In some embodiments, the enzymes can be, or can include, EC 6.1 ligases forming carbon-oxygen bonds; EC 6.2 ligases forming carbon-sulfur bonds; EC 6.3 ligases forming carbon-nitrogen bonds; EC 6.4 ligases forming carbon-carbon bonds; EC 6.5 ligases forming phosphoric ester bonds; or EC 6.6 ligases forming nitrogen-metal bonds.

In some embodiments, the enzyme can be a methyltransferase or a glycoside hydrolase. In some embodiments, the enzyme can be a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, or a xylosidase.

The number of barcoded enzymes tested can vary. In some embodiments, the number of barcoded enzymes tested can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, $10^9$, or a number or a range between any two of these values. In some embodiments, the number of barcoded enzymes tested can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, or $10^9$.

Synthetic Particles

The methods, compositions, and systems disclosed herein can utilize different types of synthetic particles, for example beads such as magnetic beads. In some embodiments, the synthetic particles can comprise beads such as magnetic beads. Non-limiting examples of the beads include silica beads, silica-like beads, silica gel beads, controlled pore glass beads, magnetic beads, Sephadex/Sepharose beads, cellulose beads, polystyrene beads, or any combination thereof, streptavidin beads, agarose beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, anti-biotin microbeads, anti-fluorochrome microbeads, BcMag™ Carboxyl-Terminated Magnetic Beads, and any combination thereof.

EXAMPLES

Example 1

Determination of the Activity of Thiopurine Methyl Transferase (TPMT)

This example demonstrates the determination of the activity and identity of the thiopurine methyl transferase using the methods disclosed herein.

A polynucleotide encoding a peptide barcoded human thiopurine methyl transferase (TPMT) was incubated for 3 hours at 37° C. in the PURExpress® cell-free transcription/translation system (New England Biolabs, Inc. (Ipswich, Mass.)) according to the manufacturer's protocol in the presence (+protease) or the absence (−protease) of the WELQut-protease. The peptide barcode had an amino acid sequence of MRPPGFSPFRWELQ (Seq ID No: 111). After cell-free transcription/translation of peptide barcoded thiopurine methyl transferase (TPMT), 1 mM 6-mercaptopurine and phosphate buffered saline (0.1×) were added with (+cofactor) or without (−cofactor) 3.2 mM of the cofactor S-adenosyl-methionine (SAM). After incubation at 37° C., 100 rpm for approximately 24 hours (no shaking), methylation of 6-mercaptopurine and the presence of peptide barcode were determined by liquid chromatography-electrospray ionization-mass spectrometry (LC-ESI-MS).

Figure 6:
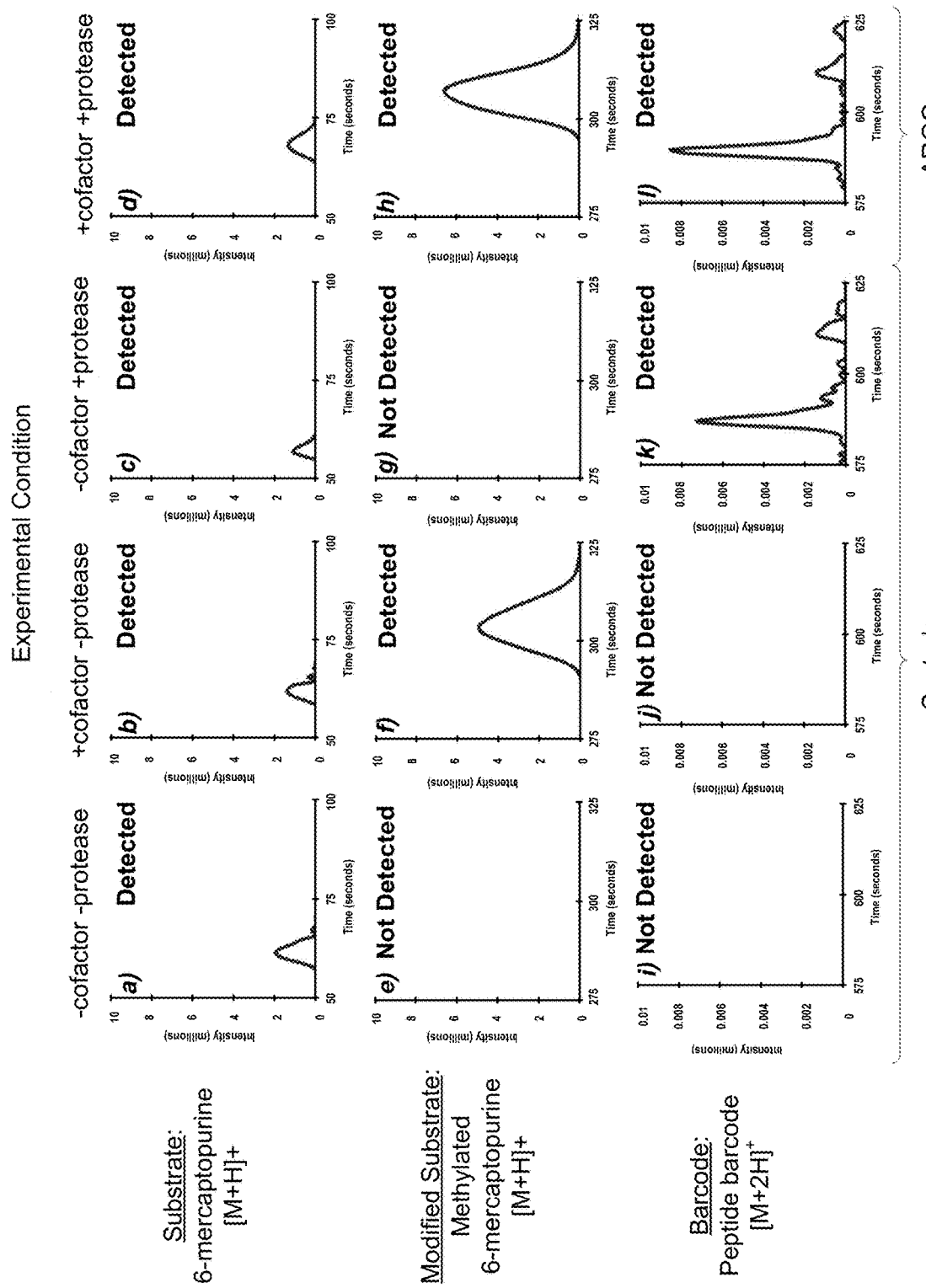
FIG. 6 shows liquid chromatography-electrospray ionization-mass spectrometry (LC-ESI-MS) plots of peptide barcoded thiopurine methyl transferase (TPMT) incubated with 6-mercaptopurine and WELQut-protease.

FIG. 6 shows liquid chromatography-electrospray ionization-mass spectrometry (LC-ESI-MS) plots of peptide barcoded thiopurine methyl transferase (TPMT) incubated with 6-mercaptopurine and WELQut-protease. FIG. 6 panels a, e, and i show that in the absence of the cofactor S-adenosyl-methionine and the absence of the WELQut-protease, no methylated 6-mercaptopurine nor peptide barcode were detected by mass spectrometry. FIG. 6 panels b, f, and j show that in the presence of the cofactor S-adenosyl-methionine and the absence of the WELQut-protease, methylated 6-mercaptopurine was detected by mass spectrometry while no peptide barcode was detected by mass spectrometry. FIG. 6 panels c, g, and k show that in the absence of the cofactor S-adenosyl-methionine and the presence of the WELQut-protease, no methylated 6-mercaptopurine was detected by mass spectrometry while the peptide barcode was detected by mass spectrometry. FIG. 6 panels d, h, and 1 show that in the presence of the cofactor S-adenosyl-methionine and the WELQut-protease, methylated 6-mercaptopurine and the peptide barcode were detected by mass spectrometry.

Altogether, these data indicate that the methods disclosed herein can be used to determine the activity and the identity of the human thiopurine methyl transferase.

Example 2

Gene Product Quantification

This example demonstrates quantification of a gene product based on a quantification peptide barcode.

Figure 7:
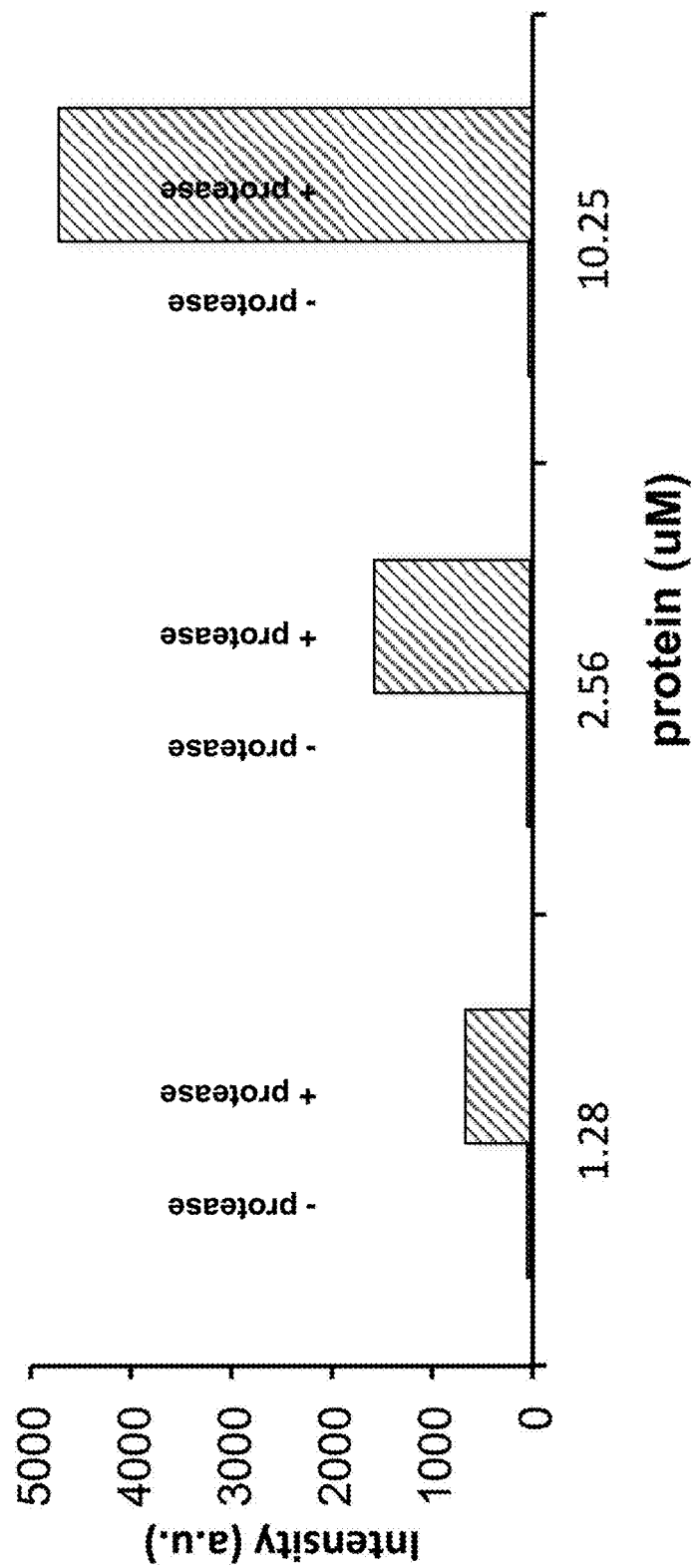
FIG. 7 is a bar chart showing quantification of peptide barcodes and gene products by matrix-assisted laser desorption/ionization (MALDI-MS).

A peptide barcode can be used for gene product quantification. By quantifying the amount of peptide barcode present, the amount of soluble gene product in a reaction can be determined because the molar ratio of the peptide barcode and the gene product can be 1:1. FIG. 7 is a bar chart showing quantification of peptide barcodes and gene products by matrix-assisted laser desorption/ionization (MALDI-MS). Different concentrations (1.28, 2.56, or 10.25 μm) of a peptide barcoded protein were incubated with WELQ-protease for ~19 hours at 18° C. The peptide barcode had an amino acid sequence of QRTFLLRNMWELQ (Seq ID No: 112). Peptide barcode quantification was determined by measuring peak areas of mass spectra determined using MALDI-MS. The average peak area (intensity in arbitrary unit (a.u)) determined is plotted against the starting concentration of the peptide barcoded protein in FIG. 7. FIG. 7 shows the linear relationship between the concentration of the peptide barcoded protein (1.28, 2.56, or 10.25 μm) and the quantities of the peptide barcode in the mass spectra. Thus, the peptide barcode can be used for gene product quantification.

Altogether, these data indicate that a peptide barcode can be used for gene product quantification.

Example 3

Determination of the Activity of β-Glucosidase

This example demonstrates the determination of the activity and identity of the β-glucosidase using the methods disclosed herein.

The glycoside hydrolase activity and the identity of the glycoside hydrolase family 1 (GH1) β-glucosidase from *Pyrococcus furiosus* were determined. The barcoded β-glucosidase was produced recombinantly using the Protein Research Kit (S) from CellFree Sciences Co., Ltd. (Ehime, Japan) according to the manufacturer's protocol. The Protein Research Kit is a wheat-germ based in vitro transcription translation system. The peptide barcode had an amino acid sequence of FLLRNWELQ (Seq ID No: 113). The barcoded β-glucosidase was purified from the in vitro transcription/translation reaction by immobilization on Dynabeads® His-Tag Isolation & Pulldown (Thermo Fisher Scientific (Waltham, Mass.)) according to the manufacturer's protocol.

The immobilized barcoded β-glucosidase was used to determine hydrolase activity. Beads containing the immobilized β-glucosidase were resuspended in phosphate buffered saline and incubated with cellobiose nanostructure-initiator mass spectrometry (NIMS) probe (substrate) and WELQut protease. In controls, one or both the WELQut protease and the substrate were omitted. Reactions were incubated for approximately 20 hours at 20° C. (no shaking). Cellobiose cleavage and the presence of peptide barcode were determined by liquid chromatography Nanostructure-Initiator Mass Spectrometry (LC-NIMS).

Figure 8:
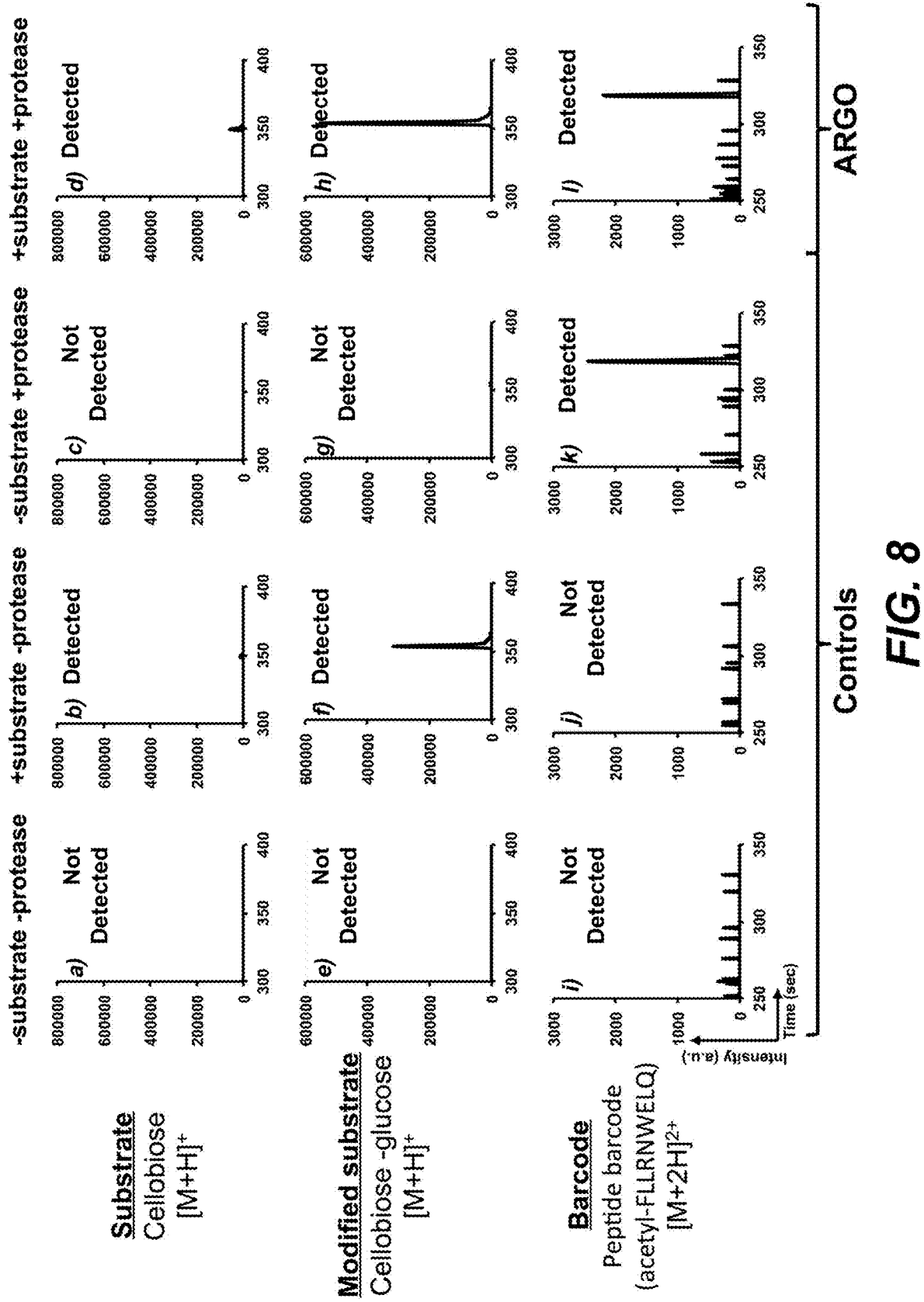
FIG. 8 shows liquid chromatography-electrospray ionization-mass spectrometry (LC-ESI-MS) plots of reactions between peptide barcoded glycoside hydrolase family 1 (GH1) β-glucosidase from *Pyrococcus furiosus* with cellobiose and WELQut-protease.

FIG. 8 show liquid chromatography-electrospray ionization-mass spectrometry (LC-ESI-MS) plots of reactions between peptide barcoded glycoside hydrolase family 1 (GH1) β-glucosidase from *Pyrococcus furiosus* with cellobiose and WELQ-protease. FIG. 8 panels a, e, and i show that in the absence of the substrate and the WELQut-protease, no cellobiose (substrate), cellobiose-glucose (modified substrate), and acetyl-FLLRNWELQ (peptide barcode) (Seq ID No: 113) were not detected by mass spectrometry. FIG. 8 panels b, f, and j show that in the presence of the substrate and the absence of the WELQut-protease, the modified substrate was detected by mass spectrometry while no peptide barcode was detected by mass spectrometry. FIG. 8 panels c, g, and k show that in the absence of the substrate and the presence of the WELQut-protease, no substrate or modified substrate were detected by mass spectrometry while the peptide barcode was detected by mass spectrometry. FIG. 8 panels d, h, and l show that in the presence of the substrate and the WELQut-protease, the modified substrate and the peptide barcode were detected by mass spectrometry.

Altogether, these data indicate that the methods disclosed herein can be used to determine the activity and the identity of the glycoside hydrolase family 1 (GH1) β-glucosidase from *Pyrococcus furiosus*.

Example 4

Recombinant Production of Glycoside Hydrolases

This example demonstrates production of glycoside hydrolases using an *E. coli* expression system.

Plasmids containing glycoside hydrolases under the transcriptional control of a T7 promoter and terminator were used. Glycoside hydrolases were expressed in Bl21(DE3) *E. coli* cultures and induced using the Overnight Express™ Autoinduction Systems (Novagen, USA). The cells were grown at 30° C. in 5 ml of overnight Express Instant TB medium with 100 μg/ml kanamycin for 16-20 hours. The cells were harvested by centrifugation (5,000×g, 15 minutes, 4° C.), and stored at −20° C. The bacterial pellets obtained were thawed at room temperature, resuspended in 1 ml CelLytic™ B Plus (Sigma-Aldrich, USA), and incubated at room temperature for 2 hours on a horizontal shaker. Cellular debris was removed by centrifugation (10,000×g, 15 minutes, 4° C.). Ni-NTA magnetic beads (Dynabeads® His-Tag Isolation & Pulldown, Thermo Fisher Scientific, USA) and 1 ml binding buffer (100 mM Sodium Phosphate, 600 mM NaCl, 0.02% Tween®-20, pH 8.0) were added to the supernatant (30 μl beads per sample). The solution was incubated at room temperature for 30 minutes on a horizontal shaker. The protein-bead mixture was collected using a magnet, and supernatant was removed. To remove unbound proteins, the beads were resuspended in 0.120 ml Wash Buffer (50 mM Sodium Phosphate, 300 mM NaCl, pH 8.0), incubated for 5 minutes, collected using a magnet, supernatant removed, and repeated trice for a total of 4 washes. The immobilized barcoded β-glucosidase was used to determine hydrolase activity.

Altogether, these data indicate that an *E. coli*-based protein expression system can be used to produce barcoded enzymes.

Example 5

Screening of Three Recombinant GH1 β-Glucosidases

This example demonstrates screening of three recombinant GH1 β-glucosidases (GH1s) using Matrix-Assisted Laser Desorption Ionization Mass Spectrometry.

Figure 9:
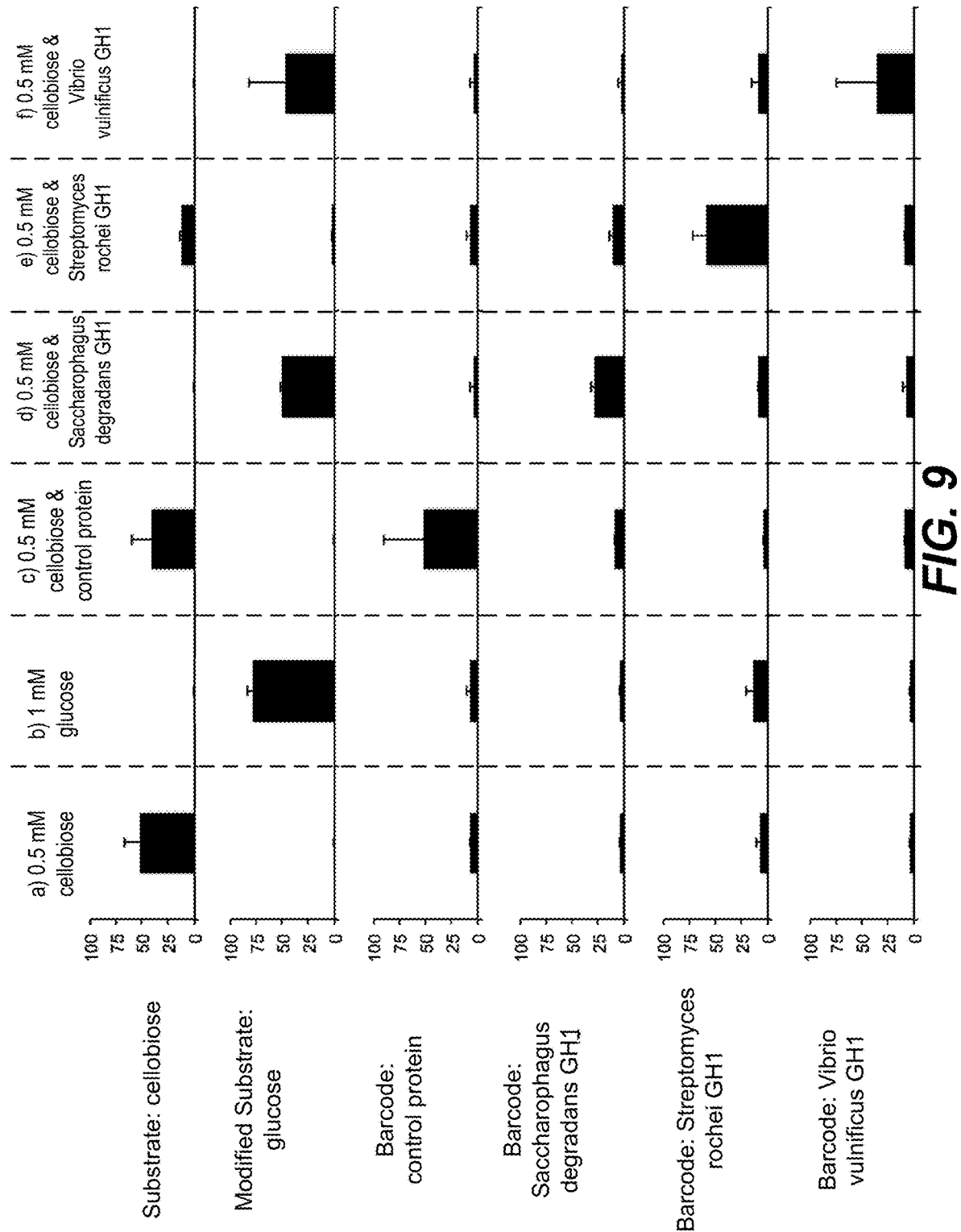
FIG. 9 show MALDI data of reactions between peptide barcoded GH1 Glycosyl Hydrolases with cellobiose and the WELQ-protease

Barcoded putative GH1s from *Saccharophagus degradans, Streptomyces rochei*, and *Vibrio vulnificus* were produced recombinantly. The recombinant GH1s from the three species were purified and immobilized on magnetic beads (Dynabeads® His-Tag Isolation & Pulldown, Life Technologies), according to manufactures' protocol. Subsequently, beads containing immobilized GH1s were resuspended in phosphate buffered saline and incubated with a substrate analog, a cellobiose NIMS probe, and the WELQ protease. In a control, a non-functional protein was incubated with the substrate analog. Reactions occurred at 20° C. for ~20 h. Then, cellobiose cleavage into glucose, the modified substrate of cellobiose, in presence of peptide barcodes, thus GH1 or the control protein, were determined by MALDI-MS (FIG. 9). FIG. 9 panel a shows that the cellobiose in a 0.5 mM sample with no GH1 or control protein was not cleaved into glucose. FIG. 9 panel b shows that glucose, the modified substrate of cellobiose, was not degraded in the absence GH1 or the control protein. FIG. 9 panels c and e show that the control protein and the *Streptomyces rochei* GH1 were unable to cleave cellobiose into glucose. FIG. 9 panels d and f show that the *Saccharophagus degradans* and *Vibrio vulnificus* GH1 were able to cleave cellobiose into glucose.

Altogether, these data show that protein activities and protein identification can be determined simultaneously based on substrate cleavage and identification peptide barcode using mass spectrometry.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for determining substrate specificity of an enzyme, comprising:
   generating a barcoded enzyme by transcription and translation of a polynucleotide encoding a barcoded enzyme which comprises the enzyme cleavably fused to a predetermined peptide barcode, wherein the polynucleotide comprises a gene encoding the enzyme fused to a nucleotide sequence encoding the predetermined peptide barcode;
   providing a sample comprising the barcoded enzyme;
   incubating the barcoded enzyme with a protease capable of removing the predetermined peptide barcode from the barcoded enzyme and one or more candidate substrates to obtain one or more modified candidate substrates in one or more reactions, wherein the barcoded enzyme is incubated with the protease prior to or during being incubated with the one or more candidate substrates, and wherein the one or more candidate substrates differ from one another by at least one functional group;
   generating a mass spectrum of each of the one or more reactions;
   determining a substrate specificity of the enzyme with respect to each of the one or more candidate substrates based on
      whether ions of each of the one or more modified candidate substrates are in the mass spectrum, and/or
      the ratio of ions of each of the one or more candidate substrates and ions of a corresponding modified candidate substrate in the mass spectrum;
   determining the identity of the barcoded enzyme in the sample by identifying ions of the predetermined peptide barcode in the mass spectrum; and
   quantifying the barcoded enzyme based on ions of the predetermined peptide barcode in the mass spectrum.

2. The method of claim 1, wherein incubating the barcoded enzyme with the protease and the one or more candidate substrates comprises adding the barcoded enzyme into a solution, wherein the solution comprises the protease and the one or more candidate substrates.

3. The method of claim 1, wherein the barcoded enzyme is incubated with some or all of the one or more candidate substrates in one of the one or more reactions, or wherein the barcoded enzyme is incubated with one of the one or more candidate substrates in one of the one or more reactions.

4. The method of claim 1, wherein volume of at least one of the one or more reactions is about 1 microliter, 1 nanoliter, 1 picoliter, or any combination thereof.

5. The method of claim 1, wherein generating the barcoded enzyme comprises:
   providing the polynucleotide encoding the barcoded enzyme; and
   incubating the polynucleotide in a cell-free transcription/translation reaction to generate the barcoded enzyme.

6. The method of claim 5, wherein the components of the cell-free transcription/translation reaction comprise a reaction buffer, a RNA polymerase, nucleotide triphosphates (NTPs), a ribonuclease inhibitor, a ribosome, aminoacyl-tRNA synthetase, tRNA, an amino acid mixture, an initiation factor, an elongation factor, a release factor, or a combination thereof.

7. The method of claim 1, wherein generating the barcoded enzyme comprises generating the barcoded enzyme using a microfluidic device.

8. The method of claim 7, wherein generating the barcoded enzyme comprises:
   generating a first droplet comprising the polynucleotide encoding the barcoded enzyme using a first microchannel of the microfluidic device;
   generating a second droplet comprising components of a cell-free transcription/translation reaction using a second microchannel of the microfluidic device;
   generating a first combined droplet comprising the polynucleotide and the components of the cell-free transcription/translation reaction from the first droplet and the second droplet using an immiscible fluid; and
   incubating the polynucleotide with the components of the cell-free transcription/translation reaction to generate the barcoded enzyme in the first combined droplet.

9. The method of claim 1, wherein incubating the barcoded enzyme with the one or more candidate substrates comprises incubating the barcoded enzyme with the one or more candidate substrates using a microfluidic device.

10. The method of claim 9, wherein incubating the barcoded enzyme with the one or more candidate substrates using the microfluidic device comprises:
    generating a first droplet comprising the barcoded enzyme using a first microchannel of the microfluidic device;
    generating a second droplet comprising the one or more candidate substrates using a second microchannel of the microfluidic device;
    generating a first combined droplet comprising the barcoded enzyme and the one or more candidate substrates from the first droplet and the second droplet using an immiscible fluidic; and
    incubating the barcoded enzyme with the one or more candidate substrates in the first combined droplet.

11. The method of claim 1, wherein each of the one or more candidate substrates differ from its corresponding modified candidate substrate by at least one functional group.

12. The method of claim 1, wherein the one or more candidate substrates comprise at least 10 substrates, 100 substrates, 1000 substrates, or any combination thereof.

13. The method of claim 1, wherein the quantity of ions of the predetermined peptide barcode in the mass spectra has a linear relationship with the concentration of the barcoded enzyme in a reaction.

14. The method of claim 1, wherein the barcoded enzyme further comprises a quantification barcode.

15. The method of claim 14, further comprising quantifying the barcoded enzyme based on ions of the quantification barcode in the mass spectrum.

16. The method of claim 15, wherein the quantity of ions of the quantification barcode in the mass spectra has a linear relationship with the concentration of the barcoded enzyme in a reaction.

* * * * *

SEQUENCE LISTING

```
<160> NUMBER OF SEQ ID NOS: 113

<210> SEQ ID NO 1
<211> LENGTH: 6
<212> TYPE: PRT
<213> ORGANISM: Artificial Sequence
<220> FEATURE:
<223> OTHER INFORMATION: note="Description of Artificial Sequence:
```

-continued

Synthetic Polypeptide"

<400> SEQUENCE: 1

Gly Thr Phe Leu Arg Asn
1               5

<210> SEQ ID NO 2
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 2

Gln Arg Trp Thr Phe Leu Leu Arg Asn
1               5

<210> SEQ ID NO 3
<211> LENGTH: 6
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 3

Gln Thr Phe Leu Arg Asn
1               5

<210> SEQ ID NO 4
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 4

Gly Thr Phe Leu Arg Asn Ser
1               5

<210> SEQ ID NO 5
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 5

Gly Thr Phe Leu Leu Arg Asn Leu
1               5

<210> SEQ ID NO 6
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 6

Asn Trp Thr Phe Leu Arg Asn
1               5

<210> SEQ ID NO 7

```
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 7

Gly Thr Phe Leu Leu Arg Asn His
1               5

<210> SEQ ID NO 8
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 8

Gly Thr Phe Leu Leu Arg Asn Phe
1               5

<210> SEQ ID NO 9
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 9

Gln Thr Phe Leu Leu Arg Asn Ile
1               5

<210> SEQ ID NO 10
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 10

Asn Thr Phe Leu Leu Arg Asn His
1               5

<210> SEQ ID NO 11
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 11

Gln Thr Phe Leu Leu Arg Asn Lys
1               5

<210> SEQ ID NO 12
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 12
```

Gln Arg Thr Phe Leu Leu Arg Asn
1               5

<210> SEQ ID NO 13
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 13

Gly Arg Thr Phe Leu Leu Arg Asn Pro
1               5

<210> SEQ ID NO 14
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 14

Gln Trp Thr Phe Leu Leu Arg Asn
1               5

<210> SEQ ID NO 15
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 15

Asn Arg Thr Phe Leu Leu Arg Asn Gly
1               5

<210> SEQ ID NO 16
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 16

Gln Arg Thr Phe Leu Leu Arg Asn Ala
1               5

<210> SEQ ID NO 17
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 17

Gln Arg Thr Phe Leu Leu Arg Asn Ile
1               5

<210> SEQ ID NO 18
<211> LENGTH: 9
<212> TYPE: PRT
<213> ORGANISM: Artificial Sequence
<220> FEATURE:

<223> OTHER INFORMATION: note="Description of Artificial Sequence:
      Synthetic Polypeptide"

<400> SEQUENCE: 18

Gln Arg Thr Phe Leu Leu Arg Asn Asn
1               5

<210> SEQ ID NO 19
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 19

Asn Arg Thr Phe Leu Leu Arg Asn Arg
1               5

<210> SEQ ID NO 20
<211> LENGTH: 6
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 20

Asn Thr Phe Leu Arg Asn
1               5

<210> SEQ ID NO 21
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 21

Gly Thr Phe Leu Arg Asn Pro
1               5

<210> SEQ ID NO 22
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 22

Gly Thr Phe Leu Arg Asn Val
1               5

<210> SEQ ID NO 23
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 23

Gly Thr Phe Leu Arg Asn Thr
1               5

```
<210> SEQ ID NO 24
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 24

Gly Thr Phe Leu Arg Asn Leu
1               5

<210> SEQ ID NO 25
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 25

Asn Thr Phe Leu Arg Asn Gly
1               5

<210> SEQ ID NO 26
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 26

Gln Thr Phe Leu Arg Asn Gly
1               5

<210> SEQ ID NO 27
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 27

Gly Thr Phe Leu Arg Asn Met
1               5

<210> SEQ ID NO 28
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 28

Gly Thr Phe Leu Arg Asn His
1               5

<210> SEQ ID NO 29
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 29
```

```
Gln Thr Phe Leu Arg Asn Ala
1               5

<210> SEQ ID NO 30
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 30

Asn Thr Phe Leu Arg Asn Ser
1               5

<210> SEQ ID NO 31
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 31

Gly Thr Phe Leu Arg Asn Phe
1               5

<210> SEQ ID NO 32
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 32

Asn Thr Phe Leu Arg Asn Pro
1               5

<210> SEQ ID NO 33
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 33

Gly Thr Phe Leu Arg Asn Arg
1               5

<210> SEQ ID NO 34
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 34

Gln Thr Phe Leu Arg Asn Ser
1               5

<210> SEQ ID NO 35
<211> LENGTH: 7
<212> TYPE: PRT
<213> ORGANISM: Artificial Sequence
```

```
<220> FEATURE:
<223> OTHER INFORMATION: note="Description of Artificial Sequence:
      Synthetic Polypeptide"

<400> SEQUENCE: 35

Gly Thr Phe Leu Arg Asn Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 36

Gln Thr Phe Leu Arg Asn Pro
1               5

<210> SEQ ID NO 37
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 37

Gln Thr Phe Leu Arg Asn Val
1               5

<210> SEQ ID NO 38
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 38

Gln Thr Phe Leu Arg Asn Thr
1               5

<210> SEQ ID NO 39
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 39

Gln Thr Phe Leu Arg Asn Leu
1               5

<210> SEQ ID NO 40
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 40

Gln Thr Phe Leu Arg Asn Asn
1               5
```

<210> SEQ ID NO 41
<211> LENGTH: 7
<212> TYPE: PRT
<213> ORGANISM: Artificial Sequence
<220> FEATURE:
<223> OTHER INFORMATION: note="Description of Artificial Sequence: Synthetic Polypeptide"

<400> SEQUENCE: 41

Gly Trp Thr Phe Leu Arg Asn
1               5

<210> SEQ ID NO 42
<211> LENGTH: 7
<212> TYPE: PRT
<213> ORGANISM: Artificial Sequence
<220> FEATURE:
<223> OTHER INFORMATION: note="Description of Artificial Sequence: Synthetic Polypeptide"

<400> SEQUENCE: 42

Asn Thr Phe Leu Arg Asn Met
1               5

<210> SEQ ID NO 43
<211> LENGTH: 7
<212> TYPE: PRT
<213> ORGANISM: Artificial Sequence
<220> FEATURE:
<223> OTHER INFORMATION: note="Description of Artificial Sequence: Synthetic Polypeptide"

<400> SEQUENCE: 43

Asn Thr Phe Leu Arg Asn His
1               5

<210> SEQ ID NO 44
<211> LENGTH: 7
<212> TYPE: PRT
<213> ORGANISM: Artificial Sequence
<220> FEATURE:
<223> OTHER INFORMATION: note="Description of Artificial Sequence: Synthetic Polypeptide"

<400> SEQUENCE: 44

Gln Thr Phe Leu Arg Asn Lys
1               5

<210> SEQ ID NO 45
<211> LENGTH: 8
<212> TYPE: PRT
<213> ORGANISM: Artificial Sequence
<220> FEATURE:
<223> OTHER INFORMATION: note="Description of Artificial Sequence: Synthetic Polypeptide"

<400> SEQUENCE: 45

Gly Thr Phe Leu Leu Arg Asn Ser
1               5

<210> SEQ ID NO 46
<211> LENGTH: 7
<212> TYPE: PRT
<213> ORGANISM: Artificial Sequence
<220> FEATURE:
<223> OTHER INFORMATION: note="Description of Artificial Sequence: Synthetic Polypeptide"

```
<400> SEQUENCE: 46

Gln Thr Phe Leu Arg Asn Met
1               5

<210> SEQ ID NO 47
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 47

Asn Thr Phe Leu Arg Asn Phe
1               5

<210> SEQ ID NO 48
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 48

Gln Thr Phe Leu Arg Asn His
1               5

<210> SEQ ID NO 49
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 49

Gly Thr Phe Leu Leu Arg Asn Pro
1               5

<210> SEQ ID NO 50
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 50

Gly Thr Phe Leu Leu Arg Asn Val
1               5

<210> SEQ ID NO 51
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 51

Asn Thr Phe Leu Arg Asn Arg
1               5

<210> SEQ ID NO 52
<211> LENGTH: 8
<212> TYPE: PRT
```

```
<213> ORGANISM: Artificial Sequence
<220> FEATURE:
<223> OTHER INFORMATION: note="Description of Artificial Sequence:
      Synthetic Polypeptide"

<400> SEQUENCE: 52

Gly Thr Phe Leu Leu Arg Asn Thr
1               5

<210> SEQ ID NO 53
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 53

Gln Thr Phe Leu Arg Asn Phe
1               5

<210> SEQ ID NO 54
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 54

Asn Thr Phe Leu Arg Asn Tyr
1               5

<210> SEQ ID NO 55
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 55

Gln Thr Phe Leu Arg Asn Arg
1               5

<210> SEQ ID NO 56
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 56

Gln Thr Phe Leu Arg Asn Tyr
1               5

<210> SEQ ID NO 57
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 57

Gln Thr Phe Leu Leu Arg Asn Gly
1               5
```

```
<210> SEQ ID NO 58
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 58

Gly Thr Phe Leu Leu Arg Asn Met
1               5

<210> SEQ ID NO 59
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 59

Gln Thr Phe Leu Leu Arg Asn Ala
1               5

<210> SEQ ID NO 60
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 60

Gln Trp Thr Phe Leu Arg Asn
1               5

<210> SEQ ID NO 61
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 61

Asn Thr Phe Leu Leu Arg Asn Pro
1               5

<210> SEQ ID NO 62
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 62

Gly Thr Phe Leu Leu Arg Asn Arg
1               5

<210> SEQ ID NO 63
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"
```

```
<400> SEQUENCE: 63

Gln Thr Phe Leu Leu Arg Asn Ser
1               5

<210> SEQ ID NO 64
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 64

Gly Thr Phe Leu Leu Arg Asn Tyr
1               5

<210> SEQ ID NO 65
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 65

Gln Thr Phe Leu Leu Arg Asn Pro
1               5

<210> SEQ ID NO 66
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 66

Gln Thr Phe Leu Leu Arg Asn Val
1               5

<210> SEQ ID NO 67
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 67

Gln Thr Phe Leu Leu Arg Asn Thr
1               5

<210> SEQ ID NO 68
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 68

Gln Thr Phe Leu Leu Arg Asn Asn
1               5

<210> SEQ ID NO 69
<211> LENGTH: 8
```

```
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 69

Gly Trp Thr Phe Leu Leu Arg Asn
1               5

<210> SEQ ID NO 70
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 70

Asn Thr Phe Leu Leu Arg Asn Met
1               5

<210> SEQ ID NO 71
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 71

Gln Thr Phe Leu Leu Arg Asn Met
1               5

<210> SEQ ID NO 72
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 72

Asn Thr Phe Leu Leu Arg Asn Phe
1               5

<210> SEQ ID NO 73
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 73

Gln Thr Phe Leu Leu Arg Asn His
1               5

<210> SEQ ID NO 74
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 74

Asn Thr Phe Leu Leu Arg Asn Arg
```

<210> SEQ ID NO 75
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 75

Gln Thr Phe Leu Leu Arg Asn Phe
1               5

<210> SEQ ID NO 76
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 76

Asn Thr Phe Leu Leu Arg Asn Tyr
1               5

<210> SEQ ID NO 77
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 77

Gln Thr Phe Leu Leu Arg Asn Tyr
1               5

<210> SEQ ID NO 78
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 78

Asn Trp Thr Phe Leu Leu Arg Asn
1               5

<210> SEQ ID NO 79
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 79

Gly Arg Thr Phe Leu Leu Arg Asn Val
1               5

<210> SEQ ID NO 80
<211> LENGTH: 9
<212> TYPE: PRT
<213> ORGANISM: Artificial Sequence
<220> FEATURE:
<223> OTHER INFORMATION: note="Description of Artificial Sequence:

Synthetic Polypeptide"

<400> SEQUENCE: 80

Gly Arg Thr Phe Leu Leu Arg Asn Ile
1               5

<210> SEQ ID NO 81
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 81

Gln Arg Thr Phe Leu Leu Arg Asn Gly
1               5

<210> SEQ ID NO 82
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 82

Gly Arg Thr Phe Leu Leu Arg Asn Met
1               5

<210> SEQ ID NO 83
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 83

Gly Arg Thr Phe Leu Leu Arg Asn His
1               5

<210> SEQ ID NO 84
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 84

Asn Arg Thr Phe Leu Leu Arg Asn Ser
1               5

<210> SEQ ID NO 85
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 85

Gly Arg Thr Phe Leu Leu Arg Asn Phe
1               5

<210> SEQ ID NO 86

```
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 86

Asn Arg Thr Phe Leu Leu Arg Asn Pro
1               5

<210> SEQ ID NO 87
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 87

Gly Arg Thr Phe Leu Leu Arg Asn Arg
1               5

<210> SEQ ID NO 88
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 88

Gln Arg Thr Phe Leu Leu Arg Asn Ser
1               5

<210> SEQ ID NO 89
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 89

Gly Arg Thr Phe Leu Leu Arg Asn Tyr
1               5

<210> SEQ ID NO 90
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 90

Gln Arg Thr Phe Leu Leu Arg Asn Pro
1               5

<210> SEQ ID NO 91
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 91
```

Gln Arg Thr Phe Leu Leu Arg Asn Val
1               5

<210> SEQ ID NO 92
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 92

Gln Arg Thr Phe Leu Leu Arg Asn Thr
1               5

<210> SEQ ID NO 93
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 93

Gly Arg Trp Thr Phe Leu Leu Arg Asn
1               5

<210> SEQ ID NO 94
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 94

Asn Arg Thr Phe Leu Leu Arg Asn Met
1               5

<210> SEQ ID NO 95
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 95

Asn Arg Thr Phe Leu Leu Arg Asn His
1               5

<210> SEQ ID NO 96
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 96

Gln Arg Thr Phe Leu Leu Arg Asn Lys
1               5

<210> SEQ ID NO 97
<211> LENGTH: 9
<212> TYPE: PRT
<213> ORGANISM: Artificial Sequence
<220> FEATURE:

```
<223> OTHER INFORMATION: note="Description of Artificial Sequence:
      Synthetic Polypeptide"

<400> SEQUENCE: 97

Gln Arg Thr Phe Leu Leu Arg Asn Met
1               5

<210> SEQ ID NO 98
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 98

Asn Arg Thr Phe Leu Leu Arg Asn Phe
1               5

<210> SEQ ID NO 99
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 99

Gln Arg Thr Phe Leu Leu Arg Asn His
1               5

<210> SEQ ID NO 100
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 100

Gln Arg Thr Phe Leu Leu Arg Asn Phe
1               5

<210> SEQ ID NO 101
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 101

Asn Arg Thr Phe Leu Leu Arg Asn Tyr
1               5

<210> SEQ ID NO 102
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 102

Gln Arg Thr Phe Leu Leu Arg Asn Arg
1               5
```

```
<210> SEQ ID NO 103
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 103

Gln Arg Thr Phe Leu Leu Arg Asn Tyr
1               5

<210> SEQ ID NO 104
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 104

Asn Arg Trp Thr Phe Leu Leu Arg Asn
1               5

<210> SEQ ID NO 105
<211> LENGTH: 4
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 105

Trp Glu Leu Gln
1

<210> SEQ ID NO 106
<211> LENGTH: 7
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 106

Glu Asn Leu Tyr Phe Gln Gly
1               5

<210> SEQ ID NO 107
<211> LENGTH: 5
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 107

Asp Asp Asp Asp Lys
1               5

<210> SEQ ID NO 108
<211> LENGTH: 4
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 108
```

```
Ile Glu Gly Arg
1

<210> SEQ ID NO 109
<211> LENGTH: 6
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 109

Leu Val Pro Arg Gly Ser
1               5

<210> SEQ ID NO 110
<211> LENGTH: 8
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 110

Leu Glu Val Leu Phe Gln Gly Pro
1               5

<210> SEQ ID NO 111
<211> LENGTH: 14
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 111

Met Arg Pro Pro Gly Phe Ser Pro Phe Arg Trp Glu Leu Gln
1               5                   10

<210> SEQ ID NO 112
<211> LENGTH: 13
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 112

Gln Arg Thr Phe Leu Leu Arg Asn Met Trp Glu Leu Gln
1               5                   10

<210> SEQ ID NO 113
<211> LENGTH: 9
<212> TYPE: PRT
<213> ORGANISM: Artificial Sequence
<220> FEATURE:
<223> OTHER INFORMATION: note="Description of Artificial Sequence:
      Synthetic Polypeptide"

<400> SEQUENCE: 113

Phe Leu Leu Arg Asn Trp Glu Leu Gln
1               5
```